(12) United States Patent
Dull

(10) Patent No.: US 6,743,812 B1
(45) Date of Patent: Jun. 1, 2004

(54) PHARMACEUTICAL COMPOSITIONS AND METHODS FOR USE

(75) Inventor: Gary Maurice Dull, Lewisville, NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 09/616,187

(22) Filed: Jul. 14, 2000

(51) Int. Cl.[7] .................... A61K 31/44; C07D 401/04
(52) U.S. Cl. .................... 514/343; 546/279.4
(58) Field of Search .............. 546/279.4; 514/343

(56) References Cited

U.S. PATENT DOCUMENTS

| | | | |
|---|---|---|---|
| 3,952,050 A | 4/1976 | Price | |
| 4,528,290 A | 7/1985 | Wong et al. | |
| 4,803,207 A | 2/1989 | White et al. | |
| 5,326,782 A | 7/1994 | Barriere et al. | |
| 5,663,356 A | 9/1997 | Ruecroft et al. | 546/300 |
| 5,723,477 A | 3/1998 | McDonald et al. | 514/340 |
| 6,025,006 A | * 2/2000 | Miller et al. | 426/564 |

FOREIGN PATENT DOCUMENTS

| | | | |
|---|---|---|---|
| WO | 9619233 | * | 6/1996 |
| WO | WO 96/20600 | | 7/1996 |

OTHER PUBLICATIONS

*Preparation of Water–Soluble Compounds Through Salt Formation*; Bradley D. Anderson and Karl P. Flora; Practice of Med. Chem., Chapter 34, pp. 739–754.
*Pharmaceutical Salts*; Stephen M. Berge, Lyle D. Bighley, and Donald C. Monkhouse; Journal of Pharmaceutical Sciences, Jan. 1977, vol. 66, No. 1, pp. 1–19.
Journal of Medicinal Chemistry, Aceto et al., vol. 22 No. 2, Date: 1979 pp. 174–177.
Journal of Catalysis, Maesen et al., vol. 182, No. 1., Date: Feb. 15, 1999 pp. 270–273.

* cited by examiner

*Primary Examiner*—Alan L. Rotman
*Assistant Examiner*—Binta Robinson
(74) *Attorney, Agent, or Firm*—Womble Carlyle Sandridge & Rice, PLLC

(57) ABSTRACT

Patients susceptible to or suffering from conditions and disorders, such as central nervous system disorders, are treated by administering to a patient in need thereof compositions that are 2,3-diacyltartaric acid salts of E-metanicotine.

9 Claims, No Drawings

PHARMACEUTICAL COMPOSITIONS AND METHODS FOR USE

BACKGROUND OF THE INVENTION

The present invention relates to pharmaceutical compositions, and particularly pharmaceutical compositions incorporating compounds that are capable of affecting nicotinic cholinergic receptors. More particularly, the present invention relates to salts of compounds capable of activating nicotinic cholinergic receptors, for example, as agonists of specific nicotinic receptor subtypes. The present invention also relates to methods for treating a wide variety of conditions and disorders, and particularly conditions and disorders associated with dysfunction of the central and autonomic nervous systems.

Nicotine has been proposed to have a number of pharmacological effects. See, for example, Pullan et al. *N. Engl. J. Med.* 330:811–815 (1994). Certain of those effects may be related to effects upon neurotransmitter release. See for example, Sjak-shie et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of serotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem Res.* 17:265 (1992). In addition, nicotine reportedly potentiates the pharmacological behavior of certain pharmaceutical compositions used for the treatment of certain disorders. See, Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., *JPET* 221: 91–96 (1982) and Hamon, *Trends in Pharmacol. Res.* 15:36.

Various nicotinic compounds have been reported as being useful for treating a wide variety of conditions and disorders. See, for example, those types of conditions and disorders set forth in Williams et al. *DN&P* 7(4):205–227 (1994), Arneric et al., *CNS Drug Rev.* 1(1):1–26 (1995), Arneric et al., *Exp. Opin. Invest. Drugs* 5(1): 79–100 (1996), Bencherif et al., *JPET* 279:1413–1421 (1996), Lippiello et al., *JPET* 279:1422–1429 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 96/31475, PCT WO 97/19059, European Patent Application 857,725, and U.S. Pat. No. 5,278,176 to Lin, U.S. Pat. No. 5,583,140 to Bencherif et al., U.S. Pat. No. 5,597,919 to Dull et al., U.S. Pat. No. 5,604,231 to Smith et al., U.S. Pat. No. 5,616,716 to Dull et al., U.S. Pat. No. 5,811,442 to Bencherif et al. and U.S. Pat. No. 5,852,041 to Cosford et al.

It is common practice for compounds, such as nicotinic compounds, to be employed and administered in the form of salts. Representative pharmaceutically acceptable salts and the properties thereof are set forth in Berge et al., *J. Pharm. Sci.,* 66: 1–19 (1977) and Anderson et al., In: *The Practice Medicinal Chemistry*, Ch. 34: 739–754 (1996). See, also, U.S. Pat. No. 3,952,050 to Price and U.S. Pat. No. 5,326,782 to Barriere et al. Representative salts of nicotinic compounds can include those organic or inorganic acid addition salts of the type set forth in U.S. Pat. No. 5,663,356 to Ruecroft et al., U.S. Pat. No. 5,861,423 to Caldwell et al. and U.S. Pat. No. 5,986,100 to Bencherif et al.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, anxiolysis, attention deficit hyperactivity disorder, depression, dyslexia, epilepsy, Huntington's chorea, hyperkinesia, mania, neuro-endocrine disorders, schizophrenia, sleep disorders, tardive dyskinesia, Tourette's syndrome, and dysregulation of food intake.

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects. It would be highly desirable to provide a pharmaceutical composition incorporating a compound which interacts with nicotinic receptors, such as those which have the potential to effect the functioning of the CNS, but which compound when employed in an amount sufficient to effect the functioning of the CNS, does not significantly effect those receptor subtypes which have the potential to induce undesirable side effects (e.g., appreciable activity at skeletal muscle sites).

SUMMARY OF THE INVENTION

The present invention relates to compositions that are 2,3-diacyltartaric acid salts of nicotinic compounds, and particularly, nicotinic compounds that are characterized as aryl substituted amines (e.g., aryl substituted olefinic amines). The preferred nicotinic compounds are characterized as metanicotine-type compounds. The present invention also relates to prodrug derivatives of the compositions of the present invention.

The present invention also relates to methods for the prevention or treatment of a wide variety of conditions or disorders, and particularly those disorders characterized by dysfunction of nicotinic cholinergic neurotransmission including disorders involving neuromodulation of neurotransmitter release, such as dopamine release. The present invention also relates to methods for the prevention or treatment of disorders, such as central nervous system (CNS) disorders, which are characterized by an alteration in normal neurotransmitter release. The present invention also relates to methods for the treatment of certain conditions (e.g., a method for alleviating pain). The methods involve administering to a subject an effective amount of a composition of the present invention.

The present invention, in another aspect, relates to a pharmaceutical composition comprising an effective amount of a salt composition incorporating a nicotinic compound. Such a pharmaceutical composition incorporates a compound which, when employed in effective amounts, has the capability of interacting with relevant nicotinic receptor sites of a subject, and hence has the capability of acting as a therapeutic agent in the prevention or treatment of a wide variety of conditions and disorders, particularly those disorders characterized by an alteration in normal neurotransmitter release. Preferred pharmaceutical compositions comprise those compositions of the present invention.

The pharmaceutical compositions of the present invention are useful for the prevention and treatment of disorders, such as CNS disorders, which are characterized by an alteration in normal neurotransmitter release. The pharmaceutical compositions provide therapeutic benefit to individuals suffering from such disorders and exhibiting clinical manifestations of such disorders in that the compounds within those compositions, when employed in effective amounts, have the potential to (i) exhibit nicotinic pharmacology and affect relevant nicotinic receptors sites (e.g., act as a pharmacological agonist to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) when employed in effective amounts do not cause appreciable adverse side effects (e.g., significant increases in blood pressure and heart rate, significant negative effects upon the gastro-intestinal tract, and significant effects upon skeletal muscle). The pharmaceutical compositions of the present invention are believed to be safe and effective with regards to prevention and treatment of a wide variety of conditions and disorders.

The foregoing and other aspects of the present invention are explained in detail in the detailed description and examples set forth below.

DETAILED DESCRIPTION OF THE INVENTION

Compounds of the present invention are diacyltartaric acid salts of aryl substituted amines. The aryl substituted amine bases of the present invention include compounds of the formula:

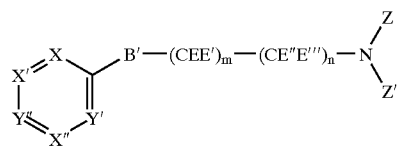

where each of X, X', X", Y' and Y" are individually nitrogen, nitrogen bonded to oxygen (e.g., an N-oxide (N—O)

functionality) or carbon bonded to a substituent species characterized as having a sigma m value greater than 0, often greater than 0.1, and generally greater than 0.2, and even greater than 0.3; less than 0 and generally less than −0.1; or 0; as determined in accordance with Hansch et al., Chem. Rev. 91:165 (1991). Preferably, less than 4, more preferably less than 3, and most preferably 1 or 2 of X, X', X", Y' and Y" are nitrogen or nitrogen bonded to oxygen. In addition, it is highly preferred that not more than 1 of X, X', X", Y' and Y" be nitrogen bonded to oxygen; and it is preferred that if one of those species is nitrogen bonded to oxygen, that species is X". Typically, X' is CR', CBr, COR', CSR' or CNR'R". Typically, X is CH. Most preferably, X" is nitrogen. In certain preferred circumstances, both X' and X" are nitrogen. Typically, Y' and Y" each are carbon bonded to a substituent species, and it is preferred that Y' and Y" both are carbon bonded to a substituent species such as hydrogen. In addition, m is an integer and n is an integer such that the sum of m plus n is 1, 2, 3, 4, 5 or 6, preferably is 1, 2, or 3, and most preferably is 2 or 3. It is highly preferred that m is 1 and n is 1. When any of X, X', X", Y' and Y" are carbon bonded to a substituent species, those substituent species often has a sigma m value between about −0.3 and about 0.75, frequently between about −0.25 and about 0.6; and each sigma m value individually can be 0 or not equal to zero.

B' is a substituted or unsubstituted two carbon atom bridging species and can be selected from the following:

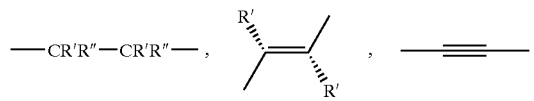

B' can be saturated or unsaturated (e.g., with R' and R") and can be part of a substituted or unsubstituted cycloalkyl ring (e.g., cyclopropyl, cyclobutyl, cyclopentyl, etc.). Substituents of B' (e.g., either R' or R") and the associated substituent species of X or Y" (i.e., when each relevant X and Y" are carbon atoms bonded to a substituent species), can combine to form a ring structure, such as a 5 or 6 membered ring structure (e.g., cycloalkyl, substituted cycloalkyl, heterocyclyl, substituted heterocyclyl). Typically, in such a circumstance, the substituent species of carbon atom of the bridging species immediately adjacent of aromatic ring combines with X or Y" to form such a ring. In addition, substituents of B', at least one of E, E', E" and E''', and the intervening atoms, can combine to form monocyclic ring structures (e.g., cycloalkyl, substituted cycloalkyl, heterocyclyl, or substituted heterocyclyl structurces) or bicyclic ring structures.

E, E', E" and E''' individually represent hydrogen, alkyl (e.g., straight chain or branched alkyl including $C_1$–$C_8$, preferably $C_1$–$C_5$, such as methyl, ethyl, or isopropyl), substituted alkyl, halo substituted alkyl (e.g., straight chain or branched alkyl including $C_1$–$C_8$, preferably $C_1$–$C_5$, such as trifluoromethyl or trichloromethyl), cycloalkyl, substituted cycloalkyl, heterocyclyl, substituted heterocyclyl, aryl, substituted aryl, alkylaryl, substituted alkylaryl, arylalkyl or substituted arylalkyl; all of E, E', E", E''' can be hydrogen, or at least one of E, E', E", E''' is non-hydrogen (e.g., alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl) and the remaining E, E', E", E''' are hydrogen; either E and E' or E" and E''' and their associated carbon atom can combine to form a ring structure such as cyclopentyl, cyclohexyl or cycloheptyl; either E and $E''$ or $E^I$ and $E^{III}$ and their associated carbon atoms can combine to form a ring structure such as cyclopentyl, cyclohexyl or cycloheptyl; Z and $Z^I$ individually represent hydrogen or alkyl (e.g., straight chain or branched alkyl including $C_1$–$C_8$, preferably $C_1$–$C_5$, such as methyl, ethyl, or isopropyl), and preferably at least one of Z and $Z^I$ is hydrogen, and most preferably Z is hydrogen and $Z^I$ is methyl; alternatively Z is hydrogen and $Z^I$ represents a ring structure (cycloalkyl, heterocyclyl, aryl or alkylaryl), such as cyclopropyl, cyclobutyl, cyclopentyl, cyclohexyl, cycloheptyl, adamantyl, quinuclidinyl, pyridinyl, quinolinyl, pyrimidinyl, phenyl, benzyl, thiazolyl or oxazolyl, methylpyridine, ethylpyridine, methylpyrazine or ethylpyrazine (where any of the foregoing can be suitably substituted with at least one substituent group, such as alkyl, alkoxyl, halo, or amino substituents); alternatively Z is hydrogen and $Z^I$ is propargyl; alternatively Z, $Z^I$, and the associated nitrogen atom can form a ring structure such as aziridinyl, azetidinyl, pyrollidinyl, piperidinyl, piperazinyl, morpholinyl, iminothiazolinyl or iminooxazolinyl (optionally substituted with pyridinyl, such as 3-pyridinyl, or pyrimidinyl, such as 5-pyrimidinyl); $Z^I$ and $E^I$ and the associated carbon and nitrogen atoms can combine to form a monocyclic ring structure such as pyrazolyl or isoxazolaminyl; $Z^I$ and $E^{III}$ and the associated carbon and nitrogen atoms can combine to form a monocyclic ring structure such as azetidinyl, pyrollidinyl, piperidinyl, thiazolyl, oxazolyl or piperazinyl or a bicyclic ring structure such as 3-([4.2.0]-2-azabicyclooctyl), 3-([2.2.2]-2azabicyclooctyl), or 3-([2.2.1]-2-azabicycloheptyl); Z, $Z^I$ and $E^{III}$ and the associated carbon and nitrogen atoms can combine to form a bicyclic ring structure such as quinuclidinyl, 2-([2.2.1]-1-azabicycloheptyl), or 2-([3.3.0]-1-azabicyclooctyl), or a tricyclic ring structure such as azaadamantyl; $Z^I$, $E^{II}$ and $E^{III}$ and the associated carbon and nitrogen atoms can combine to form a bicyclic ring structure such as 1-([2.2.1]-2-azabicycloheptyl); Z, $Z^I$, $E^{II}$ and $E^{III}$ and the associated carbon and nitrogen atoms can combine to form a tricyclic ring structure. In the situation in which B' is olefinic and its associated $R^I$ substituent combines with X or Y' to form a 5 membered heterocyclic aromatic ring (e.g., furan, pyrrole or thiophene), combinations of Z, $Z^I$, E, $E^I$, $E^{II}$ and $E^{III}$ most preferably do not combine to form a ring structure; that is, in such a situation, Z and $Z^I$ most preferably are independently hydrogen or alkyl, and although much less preferred, Z and $Z^I$ can combine with the associated nitrogen atom only to form a ring structure. More specifically, X, X', X", Y' and Y" individually include N, N—O, or an aromatic carbon atom bearing one of the following substituent species: H, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", $CF_3$, CN, $NO_2$, $C_2R'$, SH, $SCH_3$, $N_3$, $SO_2CH_3$, OR', $(CR'R'')_qOR'$, O—$(CR'R'')_qC_2R'$, SR', C(=O)NR'R", NR'C(=O)R", C(=O)R', C(=O)OR', OC(=O)R', $(CR'R'')_qOCH_2C_2R'$, $(CR'R'')_qC(=O)R'$, $(CR'R'')_qC(CHCH_3)OR'$, $O(CR'R'')_qC(=O)OR'$, $(CR'R'')_qC(=O)NR'R"$, $(CR'R'')_qNR'R"$, CH=CHR', OC(=O)NR'R" and NR'C(=O)OR" where q is an integer from 1 to 6 and R' and R" are individually hydrogen, or alkyl (e.g., $C_1$–$C_{10}$ alkyl, preferably $C_1$–$C_5$ alkyl, and more preferably methyl, ethyl, isopropyl, tertiarybutyl or isobutyl), cycloalkyl (e.g., cyclopropyl cyclobutyl, cyclopentyl, cyclohexyl, cycloheptyl and adamantyl), a non-aromatic heterocyclic ring wherein the heteroatom of the heterocyclic moiety is separated from any other nitrogen, oxygen or sulfur atom by at least two carbon atoms (e.g., quinuclidinyl, pyrollidinyl and piperidinyl), an aromatic group-containing species (e.g., pyridyl, quinolinyl, pyrimidinyl, furanyl, phenyl and benzyl where any of the foregoing can be suitably substituted with at least one substituent group, such as alkyl, hydroxyl, alkoxyl, halo, or amino substituents). Other representative aromatic ring systems are set forth in Gibson et al., *J. Med. Chem.* 39:4065 (1996). R' and R" can be straight chain or branched alkyl, or R' and R" and the intervening atoms can combine to form a ring structure (e.g., cyclopropyl cyclobutyl, cyclopentyl, cyclohexyl, cycloheptyl, adamantyl or quinuclidinyl). Substituent species to the aromatic carbon atoms previously described for X, X', X", Y' and Y", when adjacent, can combine to form one or more saturated or unsaturated, substituted or unsubstituted carbocyclic or heterocyclic rings containing, but not limited to, ether, acetal, ketal, amine, ketone, lactone, lactam, carbamate, or urea functionalities. In addition, it is highly preferred that Y' is carbon bonded to hydrogen, and it is preferred that X is C—H. Preferably, E, $E^I$ and $E^{II}$ are hydrogen. In one preferred embodiment, n is 1, m is 1 or 2, E, $E^I$ and $E^{II}$ each are hydrogen, and $E^{III}$ is alkyl (e.g., methyl). In another preferred embodiment, n is 1, m is 1 or 2 and E, $E^I$, $E^{II}$, $E^{III}$ each are hydrogen. Depending upon the identity and positioning of each individual E, $E^I$, $E^{II}$ and $E^{III}$, certain compounds can be optically active. Additionally, the aryl substituted amine component of compounds of the present invention can possess chiral centers (e.g., the compound can have an R or S configuration). Depending upon E, $E^I$, $E^{II}$ and $E^{III}$, compounds of the present invention have chiral centers, and the present invention relates to racemic mixtures of such compounds as well as single enantiomer compounds. Typically, the selection of n, m, E, $E^I$, $E^{II}$ and $E^{III}$ is such that up to about 4, and frequently up to 3, and usually 0, 1 or 2, of the substituents designated as E, $E^I$, $E^{II}$ and $E^{III}$ are non-hydrogen substituents (i.e., substituents such as alkyl or halo-substituted alkyl).

As employed herein, "alkyl" refers to straight chain or branched alkyl radicals including $C_1$–$C_8$, preferably $C_1$–$C_5$, such as methyl, ethyl, or isopropyl; "substituted alkyl" refers to alkyl radicals further bearing one or more substituent groups such as hydroxy, alkoxy, mercapto, aryl, heterocyclo, halo, amino, carboxyl, carbamyl, cyano, and the like; "alkenyl" refers to straight chain or branched hydrocarbon radicals including $C_1$–$C_8$, preferably $C_1$–$C_5$ and having at least one carbon-carbon double bond; "substituted alkenyl" refers to alkenyl radicals further bearing one or more substituent groups as defined above; "alkoxy" refers to an organo-oxy moiety, such as methoxy, isopropoxy, cyclopentyloxy, phenoxy, and the like; "cycloalkyl" refers to saturated or unsaturated cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms, such as phenyl, naphthyl, and the like; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring, such as pyridinyl, isoazolyl, tetrahydrofuranyl, and the like; and "substituted heterocyclyl" refers to heterocyclyl radicals further bearing one or more substituent groups as defined above.

Of particular interest are aryl substituted amine compounds of the formula:

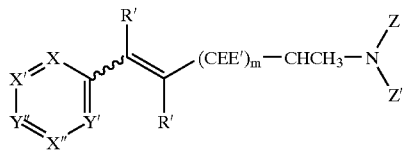

where X, X', X", Y', Y", E, E$^I$, Z, Z$^I$, m and R' are as defined hereinbefore. The wavy line in the structure indicates that the compound can have the cis (Z) or trans (E) form, preferably the trans (E) form. Preferably, both R' are hydrogen, or either or both of R' are methyl. Preferably, Z is hydrogen and Z$^I$ is hydrogen or methyl. Preferably, m is 1 or 2. Preferably, each E is hydrogen, and preferably each E$^I$ is hydrogen or methyl, but most preferably all of E and E$^I$ are hydrogen. Preferably, Y" is carbon bonded to a substituent species, and most preferably, that substituent species is hydrogen, halo, NR'R" or OR". Preferably, X" is nitrogen or carbon bonded to a substituent species such as NR'R", NO$_2$ or OR", but most preferably is nitrogen. Preferably, X' is nitrogen, but also preferably is carbon bonded to a substituent species such as hydrogen, R', halo, OR', NR'R", CN, C$_2$R' or CHCHR'. Preferably, X is carbon bonded to a substituent species, such as hydrogen.

Exemplary types of aryl substituted amine compounds are those of the type set forth in U.S. Pat. No. 5,212,188 to Caldwell et al., U.S. Pat. No. 5,604,231 to Smith et al., U.S. Pat. No. 5,616,707 to Crooks et al.; U.S. Pat. No. 5,616,716 to Dull et al., U.S. Pat. No. 5,663,356 to Ruecroft et al., U.S. Pat. No. 5,726,316 to Crooks et al., U.S. Pat. No. 5,811,442 to Bencherif et al. and U.S. Pat. No. 10 5,861,423 to Caldwell et al., and PCT WO 97/40011; 99/65876 and 00/007600; and U.S. patent application Ser. No. 09/391,747, filed Sep. 8, 1999. The foregoing references are incorporated herein by reference in their entirety for purposes of providing disclosure of representative compounds useful in carrying out the present invention.

Exemplary compounds useful in accordance with the present invention include metanicotine-type compounds. One representative preferred compound is (E)-metanicotine. Other representative preferred compounds include (2S)-(4E)-N-methyl-5-[3-(5-isopropoxypyridin)yl]-4-penten-2-amine, (3E)-N-methyl-4-[3-(5-nitro-6-aminopyridin)yl]-3-buten-1-amine, (3E)-N-methyl-4-[3-(5-(N-benzylcarboxamido)pyridin)yl]-3-buten-1-amine, (4E)-N-methyl-5-[5-(2-aminopyrimidin)yl]-4-penten-2-amine, (4E)-N-methyl-5-(3-(5-aminopyridin)yl)-4-penten-2-amine, (2S)-(4E)-N-methyl-5-[3-(5-isopropoxy-1-oxopyridin)yl)]-4-penten-2-amine, (3E)-N-methyl-4-(3-(5-isobutoxypyridin)yl)-3-buten-1-amine, (3E)-N-methyl-4-(3-(1-oxopyridin)yl)-3-buten-1-amine, (4E)-N-methyl-5-(3-(1-oxopyridin)yl)-4-penten-2-amine, (3E)-N-methyl-4-(3-(5-ethylthiopyridin)yl)-3-buten-1-amine, (4E)-N-methyl-5-(3-(5-trifluoromethylpyridin)yl)-4-penten-2-amine, (4E)-N-methyl-5-(3-(5-((carboxymethyl)oxy)pyridin)yl)-4-penten-2-amine, (4E)-5-(3-(5-isopropoxypyridin)yl)-4-penten-2-amine, and (4E)-N-methyl-5-(3-(5-hydroxypyridin)yl)-4-penten-2-amine.

The manner in which aryl substituted olefinic amine compounds of the compositions of the present invention are synthetically produced can vary.

(E)-metanicotine-type compounds can be prepared using the techniques set forth by Löffler et al., Chem. Ber., 42, pp. 3431–3438 (1909) and Laforge, J.A.C.S., 50, p. 2477 (1928) from substituted nicotine-type compounds. Certain 6-substituted metanicotine-type compounds can be prepared from the corresponding 6-substituted nicotine-type compounds using the general methods of Acheson et al., J. Chem. Soc., Perkin Trans. 1, 2, pp. 579–585 (1980). The requisite precursors for such compounds, 6-substituted nicotine-type compounds, can be synthesized from 6-substituted nicotinic acid esters using the general methods disclosed by Rondahl, Acta Pharm. Suec., 14, pp 113–118 (1977). Preparation of certain 5-substituted metanicotine-type compounds can be accomplished from the corresponding 5-substituted nicotine-type compounds using the general method taught by Acheson et al., J. Chem. Soc., Perkin Trans. 1, 2, pp. 579–585 (1980). The 5-halo-substituted nicotine-type compounds (e.g., fluoro- and bromo-substituted nicotine-type compounds) and the 5-amino nicotine-type compounds can be prepared using the general procedures disclosed by Rondahl, Act. Pharm. Suec., 14, pp.113–118 (1977). The 5-trifluoromethyl nicotine-type compounds can be prepared using the techniques and materials set forth in Ashimori et al., Chem. Pharm. Bull., 38(9), pp. 2446–2458 (1990) and Rondahl, Acta Pharm. Suec., 14, pp.113–118 (1977).

Furthermore, preparation of certain metanicotine-type compounds can be accomplished using a palladium catalyzed coupling reaction of an aromatic halide and a terminal olefin containing a protected amine substituent, removal of the protective group to obtain a primary amine, and optional alkylation to provide a secondary or tertiary amine. In particular, certain metanicotine-type compounds can be prepared by subjecting a 3-halo-substituted, 5-substituted pyridine compound or a 5-halo-substituted pyrimidine compound to a palladium catalyzed coupling reaction using an olefin possessing a protected amine functionality (e.g., such an olefin provided by the reaction of a phthalimide salt with 3-halo-1-propene, 4-halo-1-butene, 5-halo-1-pentene or 6-halo-1-hexene). See, Frank et al., J. Org. Chem., 43(15), pp.2947–2949 (1978) and Malek et al., J. Org. Chem., 47, pp. 5395–5397 (1982). Alternatively, certain metanicotine-type compounds can be prepared by coupling an N-protected, modified amino acid residue, such as 4-(N-methyl-N-tert-butyloxycarbonyl)aminobutyric acid methyl ester, with an aryl lithium compound, as can be derived from a suitable aryl halide and butyl lithium. The resulting N-protected aryl ketone is then chemically reduced to the corresponding alcohol, converted to the alkyl halide, and subsequently dehydrohalogenated to introduce the olefin functionality. Removal of the N-protecting group then affords the desired metanicotine-type compound.

There are a number of different methods for providing (Z)-metanicotine-type compounds. In one method, (Z)-metanicotine-type compounds can be synthesized from nicotine-type compounds as a mixture of E and Z isomers; and the (Z)-metanicotine-type compounds can then be separated by chromatography using the types of techniques disclosed by Sprouse et al., Abstracts of Papers, p. 32, Coresta/TCRC Joint Conference (1972). In another method, metanicotine-type compounds can be prepared by the controlled hydrogenation of the corresponding acetylenic compound (e.g., an N-methyl-4-(3-pyridinyl)-3-butyn-1-amine type compound). For example, certain 5-substituted (Z)-metanicotine-type compounds and certain 6-substituted (Z)-metanicotine-type compounds can be prepared from 5-substituted-3-pyridinecarboxaldehydes and 6-substituted- 3-pyridinecarboxaldehydes, respectively. Representative synthetic techniques for (Z)-metanicotine-type compounds are set forth in U.S. Pat. No. 5,597,919 to Dull et al. the disclosure of which is incorporated by reference in its entirety.

There are a number of methods by which the (Z)-olefinic isomers of aryl substituted olefinic amine compounds can be synthetically produced. In one approach, the (Z)-isomers of aryl substituted olefinic amine compounds can be prepared by the controlled hydrogenation of the corresponding alkynyl compounds (e.g., a N-methyl-5-(3-pyridyl)-4-butyn-2-amine-type compound) using commercially available Lindlar catalyst (Aldrich Chemical Company) using the methodology set forth in H. Lindlar et al., *Org. Syn.* 46: 89 (1966). The requisite alkynyl compounds can be prepared by the palladium catalyzed coupling of an aromatic halide, preferably a 3-bromopyridine-type or a 3-iodopyridine-type compound with an alkynyl side chain compound (e.g., an N-methyl-4-pentyn-2-amine-type compound). Typically the methodolgy set forth in L. Bleicher et al., *Synlett.* 1115 (1995) is used for the palladium catalyzed coupling of an aryl halide with a monosubstituted alkyne in the presence of copper(I) iodide and triphenylphosphine and potassium carbonate as a base. Alkynyl compounds such as N-methyl-4-pentyn-2-amine can be prepared from commercially available 4-pentyn-2-ol (Aldrich Chemical Company) by treatment with p-toluenesulfonyl chloride in pyridine, followed by reaction of the resulting 4-pentyn-2-ol p-toluenesulfonate with excess methylamine either as a 40% aqueous solution or as a 2.0 M solution in tetrahydrofuran. In some instances it may be necessary to protect the amino functionality of the N-methyl-4-pentyn-2-amine-type compound by treatment with di-tert-butyl dicarbonate to give the tert-butoxycarbonyl protected amine-type compound. Such protected amine compounds may undergo the palladium catalyzed coupling with aryl halides and the subsequent controlled hydrogenation of the resulting alkynyl compound more easily than the unprotected amine compounds. The tert-butoxycarbonyl protecting group can be easily removed using a strong acid such as trifluoroacetic acid to yield the (Z)-olefinic isomers of aryl substituted olefinic amine compounds.

The methods by which aryl substituted olefinic amine compounds of the present invention can be synthetically produced can vary. An olefinic alcohol, such as 4-penten-2-ol, is condensed with an aromatic halide, such as 3-bromopyridine or 3-iodopyridine. Typically, the types of procedures set forth in Frank et al., *J. Org. Chem.,* 43, pp. 2947–2949 (1978) and Malek et al., *J. Org. Chem.,* 47, pp. 5395–5397 (1982) involving a palladium-catalyzed coupling of an olefin and an aromatic halide are used. The olefinic alcohol optionally can be protected as a t-butyldimethylsilyl ether prior to the coupling. Desilylation then produces the olefinic alcohol. The alcohol condensation product then is converted to an amine using the type of procedures set forth in deCosta et al., *J. Org. Chem.,* 35, pp.4334–4343 (1992). Typically, the alcohol condensation product is converted to the aryl substituted olefinic amine by activation of the alcohol using methanesulfonyl chloride or p-toluenesulfonyl chloride, followed by mesylate or tosylate displacement using ammonia, or a primary or secondary amine. Thus, when the amine is ammonia, an aryl substituted olefinic primary amine compound is provided; when the amine is a primary amine such as methylamine or cyclobutylamine, an aryl substituted olefinic secondary amine compound is provided; and when the amine is a secondary amine such as dimethylamine or pyrrolidine, an aryl substituted olefinic tertiary amine compound is provided. Other representative olefinic alcohols include 4-penten-1-ol, 5-hexen-2-ol, 5-hexen-3-ol, 3-methyl-3-buten-1-ol, 2-methyl-3-buten-1-ol, 4-methyl-4-penten-1-ol, 4-methyl-4-penten-2-ol, 1-octen-4-ol, 5-methyl-1-hepten-4-ol, 4-methyl-5-hexen-2-ol, 5-methyl-5-hexen-2-ol, 5-hexen-2-ol and 5-methyl-5-hexen-3-ol. Trifluormethyl-substituted olefinic alcohols, such as 1,1,1-trifluoro-4-penten-2-ol, can be prepared from 1-ethoxy-2,2,2-trifluoro-ethanol and allyltrimethylsilane using the procedures of Kubota et al., *Tetrahedron Letters,* Vol. 33(10), pp. 1351–1354 (1992), or from trifluoroacetic acid ethyl ester and allyltributylstannane using the procedures of Ishihara et al., *Tetrahedron Letters,* Vol. 34(56), pp. 5777–5780 (1993). Certain olefinic alcohols are optically active, and can be used as enantiomeric mixtures or as pure enantiomers in order to provide the corresponding optically active forms of aryl substituted olefinic amine compounds. When an olefinic allylic alcohol, such as methallyl alcohol, is reacted with an aromatic halide, an aryl substituted olefinic aldehyde is produced; and the resulting aldehyde can be converted to an aryl substituted olefinic amine compound by reductive amination (e.g., by treatment using an alkyl amine and sodium cyanoborohydride). Preferred aromatic halides are 3-bromopyridine-type compounds and 3-iodopyridine-type compounds. Typically, substituent groups of such 3-halopyridine-type compounds are such that those groups can survive contact with those chemicals (e.g., tosylchloride and methylamine) and the reaction conditions experienced during the preparation of the aryl substituted olefinic amine compound. Alternatively, substituents such as —OH, —NH$_2$ and —SH can be protected as corresponding acyl compounds, or substituents such as —NH$_2$ can be protected as a phthalimide functionality. In the case of a dihaloaromatic, sequential palladium-catalyzed (Heck-type) couplings to two different olefinic side chains are possible.

The manner in which certain aryl substituted olefinic amine compounds possessing a branched side chain, such as (4E)-N-methyl-5-(5-isopropoxy-3-pyridyl)-4-penten-2-amine, are provided can vary. By using one synthetic approach, the latter compound can be synthesized in a convergent manner, in which the side chain, N-methyl-N-(tert-butoxycarbonyl)-4-penten-2-amine is coupled with the 3-substituted 5-halo-substituted pyridine, 5-bromo-3-isopropoxypyridine, under Heck reaction conditions, followed by removal of the tert-butoxycarbonyl protecting group. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used. The required N-methyl-N-(tert-butoxycarbonyl)-4-penten-2-amine can be synthesized as follows: (i) Commercially available 4-penten-2-ol (Aldrich Chemical Company, Lancaster Synthesis Inc.) can be treated with p-toluenesulfonyl chloride in pyridine to yield 4-penten-2-ol p-toluenesulfonate, previously described by T. Michel, et al., *Liebigs Ann.* 11: 1811 (1996). (ii) The resulting tosylate can be heated with 20 molar equivalents of methylamine as a 40% aqueous solution to yield N-methyl-4-penten-2-amine. (iii) The resulting amine, such as previously mentioned by A. Viola et al., *J. Chem. Soc., Chem. Commun.* (21): 1429 (1984), can be allowed to react with 1.2 molar equivalents of di-tert-butyl dicarbonate in dry tetrahydrofuran to yield the side chain, N-methyl-N-(tert-butoxycarbonyl)-4-penten-2-amine. The halo-substituted pyridine (e.g., 5-bromo-3-isopropoxypyridine), can be synthesized by two different routes. In one preparation, 3,5-dibromopyridine is heated at 140° C. for 14 hours with 2 molar equivalents of potassium isopropoxide in dry isopropanol in the presence of copper powder (5%, w/w of the 3,5-dibromopyridine) in a sealed glass tube to yield 5-bromo-3-isopropoxypyridine. A second preparation of 5-bromo-3-isopropoxypyridine from 5-bromonicotinic acid can be performed as follows: (i) 5-Bromonicotinic acid is converted to 5-bromonicotinamide by treatment with thionyl chloride, followed by reaction of the intermediate acid chloride with aqueous ammonia. (ii) The resulting 5-bromonicotinamide, previously described by C. V. Greco et al., *J. Heteocyclic Chem.* 7(4): 761 (1970), is subjected to Hofmann degradation by treatment with sodium hydroxide and a 70% solution of calcium hypochlorite. (iii) The resulting 3-amino-5-bromopyridine, previously described by C. V. Greco et al., *J. Heteocyclic Chem.* 7(4): 761 (1970), can be converted to 5-bromo-3-isopropoxypyridine by diazotization with isoamyl nitrite under acidic conditions, followed by treatment of the intermediate diazonium salt with isopropanol to yield 5-bromo-3-isopropoxypyridine. The palladium-catalyzed coupling of 5-bromo-3-isopropoxypyridine and N-methyl-N-(tert-butoxycarbonyl)-4-penten-2-amine is carried out in acetonitrile-triethylamine (2:1, v,v) using a catalyst consisting of 1 mole % palladium(II) acetate and 4 mole % tri-o-tolylphosphine. The reaction can be carried out by heating the components at 80° C. for 20 hours to yield (4E)-N-methyl-N-(tert-butoxycarbonyl)-5-(5-isopropoxy-3-pyridyl)-4-penten-2-amine. Removal of the tert-butoxycarbonyl protecting group can be accomplished by treatment with 30 molar equivalents of trifluoroacetic acid in anisole at 0° C. to afford (4E)-N-methyl-5-(5-isopropoxy-3-pyridyl)-4-penten-2-amine. A variety of N-methyl-5-(5-alkoxy or 5-aryloxy-3-pyridyl)-4-penten-2-amines are available from 3,5-dibromopyridine using this type of technology (i.e., treatment with sodium or potassium alkoxides or aryloxides and subsequent Heck coupling and deprotection).

The manner in which certain aryl substituted olefinic amine compounds possessing a branched side chain are provided can vary. Using one synthetic approach, a compound such as (4E)-N-methyl-5-(5-methoxy-3-pyridyl)-4-penten-2-amine can be synthesized by coupling a halo-substituted pyridine, 5-bromo-3-methoxypyridine with an olefin containing a secondary alcohol functionality, 4-penten-2-ol, under Heck reaction conditions; and the resulting pyridyl alcohol intermediate can be converted to its p-toluenesulfonate ester, followed by treatment with methylamine. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used. The required halo-substituted pyridine, 5-bromo-3-methoxypyridine is synthesized using methodology similar to that described by H. J. den Hertog et al., *Recl. Trav. Chim. Pays-Bas* 67:377 (1948), namely by heating 3,5-dibromopyridine with 2.5 molar equivalents of sodium methoxide in dry methanol in the presence of copper powder (5%, w/w of the 3,5-dibromopyridine) in a sealed glass tube at 150° C. for 14 hours to produce 5-bromo-3-methoxypyridine. The resulting 5-bromo-3-methoxypyridine, previously described by D. L. Comins, et al., *J. Org. Chem.* 55: 69 (1990), can be coupled with 4-penten-2-ol in acetonitrile-triethylamine (1:1:1, v/v) using a catalyst consisting of 1 mole % palladium(II) acetate and 4 mole % tri-o-tolylphosphine. The reaction is carried out by heating the components in a sealed glass tube at 140° C. for 14 hours to yield (4E)-N-methyl-5-(5-methoxy-3-pyridyl)-4-penten-2-ol. The resulting alcohol is treated with 2 molar equivalents of p-toluenesulfonyl chloride in dry pyridine at 0° C. to produce (4E)-N-methyl-5-(5-methoxy-3-pyridyl)-4-penten-2-ol p-toluensulfonate. The tosylate intermediate is treated with 120-molar equivalents of methylamine as a 40% aqueous solution, containing a small amount of ethanol as a co-solvent to produce (4E)-N-methyl-5-(5-methoxy-3-pyridyl)-4-penten-2-amine. When 3,5-dibromopyridine is submitted to Heck coupling with N-methyl-N-(tert-butoxycarbonyl)-4-penten-2-amine, under conditions described above, N-methyl-N-(tert-butoxycarbonyl)-5-(5-bromo-3-pyridyl)-4-penten-2-amine is produced. This can be coupled in a subsequent Heck reaction with styrene and deprotected (removal of the tert-butoxycarbonyl group), as described previously, to give (4E)-N-methyl-5-[3-(5-trans-beta-styrylpyridin)yl]-4-penten-2-amine. Similar second coupling with ethynylbenzene, and subsequent deprotection, will give (4E)-N-methyl-5-[3-(5-phenylethynylpyridin)yl]-4-penten-2-amine.

The manner in which optically active forms of certain aryl substituted olefinic amine compounds, such as (2S)-(4E)-N-methyl-5-(3-pyridyl)-4-penten-2-amine, are provided can vary. In one synthetic approach, the latter type of compound is synthesized by coupling a halo-substituted pyridine, 3-bromopyridine, with an olefin possessing a chiral, secondary alcohol functionality, (2R)-4-penten-2-ol, under Heck reaction conditions. The resulting chiral pyridyl alcohol intermediate, (2R)-(4E)-5-(3-pyridyl)-4-penten-2-ol is converted to its corresponding p-toluenesulfonate ester, which is subsequently treated with methylamine, resulting in tosylate displacement with inversion of configuration. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an aromatic halide and an olefin are used. The chiral side chain, (2R)-4-penten-2-ol can be prepared by treatment of the chiral epoxide, (R)-(+)-propylene oxide (commercially available from Fluka Chemical Company) with vinylmagnesium bromide in tetrahydrofuran at low temperatures (−25 to −10° C.) using the general synthetic methodology of A. Kalivretenos, J. K. Stille, and L. S. Hegedus, *J. Org. Chem.* 56: 2883 (1991), to afford (2R)-4-penten-2-ol. The resulting chiral alcohol is subjected to a Heck reaction with 3-bromopyridine in acetonitrile-triethylamine (1:1, v/v) using a catalyst consisting of 1 mole % palladium(II) acetate and 4 mole % tri-o-tolylphosphine. The reaction is done by heating the components at 140° C. for 14 hours in a sealed glass tube, to produce the Heck reaction product, (2R)-(4E)-5-(3-pyridyl)-4-penten-2-ol. The resulting chiral pyridyl alcohol is treated with 3 molar equivalents of p-toluenesulfonyl chloride in dry pyridine at 0° C., to afford the tosylate intermediate. The p-toluenesulfonate ester is heated with 82 molar equivalents of methylamine as a 40% aqueous solution, containing a small amount of ethanol as a co-solvent, to produce (2S)-(4E)-N-methyl-5-(3-pyridyl)-4-penten-2-amine.

In a similar manner, the corresponding aryl substituted olefinic amine enantiomer, such as (2R)-(4E)-N-methyl-5-(3-pyridyl)-4-penten-2-amine, can be synthesized by the Heck coupling of 3-bromopyridine and (2S)-4-penten-2-ol. The resulting intermediate, (2S)-(4E)-5-(3-pyridyl)-4-penten-2-ol, is converted to its p-toluenesulfonate, which is subjected to methylamine displacement. The chiral alcohol, (2S)-4-penten-2-ol, is prepared from (S)-(−)-propylene oxide (commercially available from Aldrich Chemical Company) using a procedure analogous to that described for the preparation of (2R)-4-penten-2-ol from (R)-(+)-propylene oxide as reported by A. Kalivretenos, J. K. Stille, and L. S. Hegedus, *J. Org. Chem.* 56: 2883 (1991).

In another approach to compounds of the present invention, such compounds as (3E)-N-methyl-4-(3-(6-aminopyridin)yl)-3-buten-1-amine can be prepared by subjecting a 3-halo-substituted pyridine such as 2-amino-5-bromopyridine (Aldrich Chemical Company) to a palladium-catalyzed coupling reaction with an olefin possessing a protected amine functionality, such as N-methyl-N-(3-buten-1-yl)benzamide. Removal of the benzoyl-protecting group from the resulting Heck reaction product can be accomplished by heating with aqueous acid to give (3E)-N-methyl-4-(3-(6-aminopyridin)yl)-3-buten-1-amine. The required olefin, N-methyl-N-(3-buten-1-yl)benzamide, can be prepared by reacting 4-bromo-1-butene with an excess of condensed methylamine in N,N-dimethylformamide in the presence of potassium carbonate to give N-methyl-3-buten-1-amine. Treatment of the latter compound with benzoyl chloride in dichloromethane containing triethylamine affords the olefinic side chain, N-methyl-N-(3-buten-1-yl)benzamide.

Compounds of the present invention may contain an azacyclic functionality, such as pyrrolidine or quinuclidine. The methods of synthesis of such compounds may vary. In one method, the Heck reaction can be used for the coupling a vinyl-substituted or allyl-substituted nitrogen heterocycle to a 3-halopyridine. For example, N-(tert-butoxycarbonyl)-2-allylpyrrolidine and 3-bromopyridine (Aldrich Chemical Company) can be coupled under conditions described by W. C. Frank et al., *J. Org. Chem.* 43: 2947 (1978) and N. J. Malek et al., *J. Org. Chem.* 47: 5395 (1982) involving palladium catalysis. Removal of the protecting group, using trifluoroacetic acid, will give 2-(3-(3-pyridyl)-(2E)-propen-1-yl)pyrrolidine. The requisite N-(tert-butoxycarbonyl)-2-allylpyrrolidine can be prepared from commercially available 2-pyrrolidinemethanol (Aldrich Chemical Company). Treatment of 2-pyrrolidinemethanol with di-tert-butyl dicarbonate results in protection of the amine as its tert-butoxycarbonyl derivative. Subsequent reaction with p-toluenesulfonyl chloride in pyridine, followed by sodium iodide in acetone, gives 2-(iodomethyl)-N-(tert-butoxycarbonyl)pyrrolidine. This compound can be coupled with vinylmagnesium bromide in the presence of cuprous iodide to give N-(tert-butoxycarbonyl)-2-allylpyrrolidine. The use of enantiomerically pure 2-pyrrolidinemethanol (both R and S isomers are available from Aldrich Chemical Company) results in the preparation of each enantiomer of N-(tert-butoxycarbonyl)-2-allylpyrrolidine. Subsequent reactions as outlined above results in the preparation of each enantiomer of 2-(3-(3-pyridyl)-(2E)-propen-1-yl)pyrrolidine. The secondary amino compounds can be N-methylated using aqueous formaldehyde and sodium cyanoborohydride using methodology similar to that described by M. A. Abreo et al., *J. Med. Chem.* 39:817–825 (1996) to afford each enantiomer of 2-(3-(3-pyridyl)-(2E)-propen-1-yl)-1-methylpyrrolidine.

Similarly, 2-allylquinuclidine can be coupled with 3-bromopyridine, under Heck conditions, to give 2-(3-(3-pyridyl)-(2E)-propen-1-yl)quinuclidine. The required 2-allylquinuclidine can be prepared from 3-quinuclidinone (Aldrich Chemical Company) by alkylation and deoxygenation. Thus, 3-quinuclidinone can be converted into its isopropylimine with isopropylamine and molecular sieves. Treatment of the imine with lithium diisopropylamide and allyl bromide, followed by hydrolysis, gives 2-allyl-3-quinuclidinone. Deoxygenation, by conversion of the ketone into its p-toluenesulfonylhydrazone and reduction with sodium borohydride, gives 2-allylquinuclidine.

Compounds of the present invention may contain a pyrazine or pyridazine ring. Using procedures reported M. Hasegawa, et al. (European Patent Application 561409 A2 921202), 2-methylpyrazine or 3-methylpyridazine (both available from Aldrich Chemical Company) can be condensed with N-methyl-N-(tert-butoxycarbonyl)-3-aminobutanal to give (4E)-N-methyl-N-(tert-butoxycarbonyl)-5-(2-pyrazinyl)-4-penten-2-amine and (4E)-N-methyl-N-(tert-butoxycarbonyl)-5-(3-pyridazinyl)-4-penten-2-amine respectively. Removal of the tert-butoxycarbonyl group with trifluoroacetic acid will produce (4E)-N-methyl-5-(2-pyrazinyl)-4-penten-2-amine and (4E)-N-methyl-5-(3-pyridazinyl)-4-penten-2-amine respectively. The requisite N-methyl-N-(tert-butoxycarbonyl)-3-aminobutanal can be produced from the corresponding alcohol using techniques described by M. Adamczyk and Y. Y. Chen in PCT International Application WO 9212122. The alcohol, N-methyl-N-(tert-butoxycarbonyl)-3-amino-1-butanol, can be made from commercially available 4-hydroxy-2-butanone (Lancaster Synthesis, Inc.) by sequential reductive amination (with methylamine and sodium cyanoborohydride, using chemistry reported by R. F. Borch in *Org. Syn.* 52, 124 (1974)) and protection with di-tert-butyl dicarbonate.

The manner in which certain compounds of the present invention are prepared can vary. For example, compounds that possess certain fused-ring heterocycles can be prepared by the Heck reaction. Such compounds can be synthesized by the palladium-catalyzed coupling of a bromo heterocyclic compound, such as 6-bromo-2-methyl-1H-imidazo[4,5-b]pyridine with the previously mentioned olefinic amine side chain, N-methyl-N-(tert-butoxycarbonyl)-4-penten-2-amine. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used for the coupling reaction. The resulting tert-butoxycarbonyl-protected (Boc-protected) intermediate can be subjected to treatment with a strong acid, such as trifluoroacetic acid to produce (4E)-N-methyl-5-(6-(2-methyl-1H-imidazo[4,5-b]pyridin)yl)-4-penten-2-amine. The requisite bromo-imidazopyridine, 6-bromo-2-methyl-1H-imidazo[4,5-b]pyridine can be prepared in 82% yield by heating 2,3-diamino-5-bromopyridine with acetic acid in polyphosphoric acid according to the methods described by P. K. Dubey et al., *Indian J. Chem.* 16B(6):531–533 (1978). 2,3-Diamino-5-bromopyridine can be prepared in 97% yield by heating 2-amino-5-bromo-3-nitropyridine (commercially available from Aldrich Chemical Company and Lancaster Synthesis, Inc) with tin(II) chloride dihydrate in boiling ethanol according to the techniques described by S. X. Cai et al., *J. Med. Chem.* 40(22): 3679–3686 (1997).

In another example, a bromo fused-ring heterocycle, such as 6-bromo-1,3-dioxolo[4,5-b]pyridine can be coupled with the previously mentioned olefinic amine side chain, N-methyl-N-(tert-butoxycarbonyl)-4-penten-2-amine using the Heck reaction. The resulting Boc-protected intermediate can be deprotected with a strong acid such as trifluoroacetic acid to produce (4E)-N-methyl-5-(6-(1,3-dioxolo[4,5-b]pyridin)yl)-4-penten-2-amine. The requisite bromo compound, 6-bromo-1,3-dioxolo[4,5-b]pyridine can be synthesized from 5-bromo-2,3-dihydroxypyridine, also known as 5-bromo-3-hydroxy-2(1H)-pyridinone, via a methylenation procedure using bromochloromethane, in the presence of potassium carbonate and N,N-dimethylformamide according to the methodology of F. Dallacker et al., *Z. Naturforsch.* 34 b:1729–1736 (1979). 5-Bromo-2,3-dihydroxypyridine can be prepared from furfural (2-furaldehyde, commercially available from Aldrich Chemical Company and Lancaster Synthesis, Inc) using the methods described in F. Dallacker et al., *Z. Naturforsch.* 34 b:1729–1736 (1979). Alternatively, 5-bromo-2,3-dihydroxypyridine can be prepared according to the techniques described in EP 0081745 to D. Rose and N. Maak.

In an another example of a compound that possesses a fused-ring heterocycle, the bromo compound, 7-bromo-2,3-dihydro-1,4-dioxino[2,3-b]pyridine (also known as 7-bromo-5-aza-4-oxachromane) can be condensed with the previously mentioned olefinic amine side chain, N-methyl-N-(tert-butoxycarbonyl)-4-penten-2-amine using the Heck reaction. The resulting Boc-protected compound can be deprotected with strong acid such as trifluoroacetic acid to produce (4E)-N-methyl-5-(7-(2,3-dihydro-1,4-dioxino[2,3-b]pyridin)yl-4-penten-2-amine. The required bromo compound, 7-bromo-2,3-dihydro-1,4-dioxino[2,3-b]pyridine, can be prepared by treating 5-bromo-2,3-dihydroxypyridine with 1,2-dibromoethane and potassium carbonate in N,N-dimethylformamide according to the methodology of F. Dallacker et al., *Z. Naturforsch.* 34 b: 1729–1736 (1979). 5-Bromo-2,3-dihydroxypyridine can be prepared from furfural as described above.

Other polycyclic aromatic compounds of the present invention can be prepared by the Heck reaction. Thus, certain compounds can be synthesized by the palladium-catalyzed coupling of a bromo fused-ring heterocycle, such as 6-bromo-1H-imidazo[4,5-b]pyridine-2-thiol with the previously mentioned olefinic amine side chain, N-methyl-N-(tert-butoxycarbonyl)-4-penten-2-amine. The Boc-protected intermediate, resulting from the Heck reaction, can be subjected to treatment with a strong acid, such as trifluoroacetic acid to produce (4E)-N-methyl-5-(6-(2-thio-1H-imidazo[4,5-b]pyridin)yl)-4-penten-2-amine. The requisite bromo compound, 6-bromo-1H-imidazo[4,5-b]pyridine-2-thiol can be prepared by treating 6-bromo-1H-imidazo[4,5-b]pyridine with sulfur at 230–260° C. according to the methods described in Y. M. Yutilov, *Khim. Geterotsikl Doedin.* 6: 799–804 (1988). 6-Bromo-1H-imidazo[4,5-b]pyridine can be obtained from Sigma-Aldrich Chemical Company. Alternatively, 6-bromo-1H-imidazo[4,5-b]pyridine can be prepared by treating 2,3-diamino-5-bromopyridine with formic acid in polyphosphoric acid using methodology similar to that described by P. K. Dubey et al., *Indian J. Chem.* 16B(6):531–533 (1978). 2,3-Diamino-5-bromopyridine can be prepared in 97% yield by heating 2-amino-5-bromo-3-nitropyridine (commercially available from Aldrich Chemical Company and Lancaster Synthesis, Inc) with tin(II) chloride dihydrate in boiling ethanol according to the techniques described by S. X. Cai et al., *J. Med. Chem.*, 40(22): 3679–3686 (1997). Alternatively, 6-bromo-1H-imidazo[4,5-b]pyridine-2-thiol can be prepared by heating 2,3-diamino-5-bromopyridine with $K^+$ $^-SCSOEt$ in aqueous ethanol using methodology similar to that described by T. C. Kuhler et al.,*J. Med Chem.* 38(25): 4906–4916 (1995). 2,3-Diamino-5-bromopyridine can be prepared from 2-amino-5-bromo-3-nitropyridine as described above.

In a related example, 6-bromo-2-phenylmethylthio-1H-imidazo[4,5-b]pyridine can be coupled via Heck reaction with the previously mentioned olefinic amine side chain, N-methyl-N-(tert-butoxycarbonyl)-4-penten-2-amine. The resulting Boc-protected intermediate can be subjected to treatment with a strong acid, such as trifluoroacetic acid to produce (4E)-N-methyl-5-(6-(2-phenylmethylthio-1H-imidazo[4,5-b]pyridin)yl)-4-penten-2-amine. The required bromo compound, 6-bromo-2-phenylmethylthio-1H-imidazo[4,5-b]pyridine can be prepared by alkylating the previously described 6-bromo-1H-imidazo[4,5-b]pyridine-2-thiol with benzyl bromide in the presence of potassium carbonate and N,N-dimethylformamide.

In another example, 6-bromooxazolo[4,5-b]pyridine, when submitted sequentially to palladium catalyzed coupling to N-methyl-N-(tert-butoxycarbonyl)-4-penten-2-amine and deprotection with trifluoroacetic acid, gives (4E)-N-methyl-5-(6-oxazolo[4,5-b]pyridinyl)-4-penten-2-amine. The requisite 6-bromooxazolo[4,5-b]pyridine can be produced from 2-amino-5-bromo-3-pyridinol by condensation with formic acid or a trialkyl orthoformate, using methodology similar to that of M—C. Viaud et al., *Heterocycles* 41: 2799–2809 (1995). The use of other carboxylic acids produces 2-substituted-6-bromooxazolo[4,5-b]pyridines, which are also substrates for the Heck reaction. The synthesis of 2-amino-5-bromo-3-pyridinol proceeds from furfurylamine (Aldrich Chemical Company). Thus, 5-bromo-3-pyridinol (produced from furfurylamine according to U.S. Pat. No. 4,192,946) can be chlorinated, using methods described by V. Koch et al., *Synthesis,* 499 (1990), to give 2-chloro-5-bromo-3-pyridinol, which in turn can be converted to 2-amino-5-bromo-3-pyridinol by treatment with ammonia.

5-Bromooxazolo[5,4-b]pyridine, isomeric by orientation of ring fusion to the previously described 6-bromooxazolo[4,5-b]pyridine, can also be used in the Heck coupling with N-methyl-N-(tert-butoxycarbonyl)-4-penten-2-amine. Subsequent removal of the tert-butoxycarbonyl protecting group provides (4E)-N-methyl-5-(5-oxazolo[5,4-b]pyridinyl)-4-penten-2-amine. The required 5-bromooxazolo[5,4-b]pyridine is synthesized from 3-amino-5-bromo-2-pyridinol (3-amino-5-bromo-2-pyridone) by the condensation with formic acid (or a derivative thereof) as described above. 3-Amino-5-bromo-2-pyridinol can be made by bromination (using techniques described by T. Batkowski, *Rocz. Chem.* 41: 729–741 (1967)) and subsequent tin(II) chloride reduction (according to the method described by S. X. Cai et al., *J. Med. Chem.* 40(22): 3679–3686 (1997)) of commercially available 3-nitro-2-pyridinol (Aldrich Chemical Company).

Other polycyclic aromatic compounds of the present invention can be prepared by the Heck reaction. Thus both 5-bromofuro[2,3-b]pyridine and 5-bromo-1H-pyrrolo[2,3-b]pyridine can undergo palladium catalyzed coupling with the previously described olefinic amine side chain, N-methyl-N-(tert-butoxycarbonyl)-4-penten-2-amine, to give (4E)-N-methyl-N-(tert-butoxycarbonyl)-5-(5-furo[2,3-b]pyridinyl)-4-penten-2-amine and (4E)-N-methyl-N-(tert-butoxycarbonyl)-5-(5-1H-pyrrolo[2,3-b]pyridinyl)-4-penten-2-amine respectively. Subsequent removal of the tert-butoxycarbonyl group with trifluoroacetic acid will provide (4E)-N-methyl-5-(5-furo[2,3-b]pyridinyl)-4-penten-2-amine and (4E)-N-methyl-5-(5-1H-pyrrolo[2,3-b]pyridinyl)-4-penten-2-amine. The requisite 5-bromofuro[2,3-b]pyridine and 5-bromo-1H-pyrrolo[2,3-b]pyridine can be made from 2,3-dihydrofuro[2,3-b]pyridine and 2,3-dihydropyrrolo[2,3-b]pyridine respectively, by bromination (bromine and sodium bicarbonate in methanol) and dehydrogenation (2,3-dichloro-5,6-dicyano-1,4-benzoquinone), using chemistry described by E. C. Taylor et al., *Tetrahedron* 43: 5145–5158 (1987). 2,3-Dihydrofuro[2,3-b]pyridine and 2,3-dihydropyrrolo[2,3-b]pyridine are, in turn, made from 2-chloropyrimidine (Aldrich Chemical Company), as described by A. E. Frissen et al., *Tetrahedron* 45: 803–812 (1989), by nucleophilic displacement of the chloride (with the sodium salt of 3-butyn-1-ol or with 4-amino-1-butyne) and subsequent intramolecular Diels-Alder reaction. Using similar chemistry, 2,3-dihydrofuro[2,3-b]pyridine and 2,3-dihydropyrrolo[2,3-b]pyridine are also produced from 3-methylthio-1,2,4-triazene (E. C. Taylor et al., *Tetrahedron* 43: 5145–5158 (1987)), which in turn is made from glyoxal and S-methylthiosemicarbazide (W. Paudler et al., *J. Heterocyclic Chem.* 7: 767–771 (1970)).

Brominated dihydrofuropyridines, dihydropyrrolopyridines, and dihydropyranopyridines are also substrates for the palladium catalyzed coupling. For instance, both 5-bromo-2,3-dihydrofuro[2,3-b]pyridine and 5-bromo-2,3-dihydropyrrolo[2,3-b]pyridine (from bromination of 2,3-dihydrofuro[2,3-b]pyridine and 2,3-dihydropyrrolo[2,3-b]pyridine, as described above) can be coupled with the previously mentioned olefinic amine side chain in a Heck process. Subsequent deprotection gives the corresponding (4E)-N-methyl-5-(5-(2,3-dihydrofuro[2,3-b]pyidin)yl)-4-penten-2-amine and (4E)-N-methyl-5-(5-(2,3-dihydropyrrolo[2,3-b]pyridin)yl)-4-penten-2-amine. Similar treatment of 6-bromo-2,3-dihydrofuro[3,2-b]pyridine (isomeric at the ring fusion with the [2,3-b] system) will provide (4E)-N-methyl-5-(6-(2,3-dihydrofuro[3,2-b]pyridn)yl)-4-penten-2-amine. The requisite 6-bromo-2,3-dihydrofuro[3,2-b]pyridine can be made from 5-bromo-2-methyl-3-pyridinol by sequential treatment with two equivalents of lithium diisopropylamide (to generate the 2-methylenyl, 3-oxy dianion) and one equivalent of dibromomethane. Alternatively, using chemistry similar to that described by M. U. Koller et al., *Synth. Commun.* 25: 2963–74 (1995), the silyl-protected pyridinol (5-bromo-2-methyl-3-trimethylsilyloxypyridine) can be treated sequentially with one equivalent of lithium diisopropylamide and an alkyl or aryl aldehyde to produce a 2-(2-(1-alkyl- or 1-aryl-1-hydroxy)ethyl)-5-bromo-3-(trimethylsilyloxy)pyridine. Such materials can be converted, by methods (such as acid catalyzed cyclization or the Williamson synthesis) known to those skilled in the art, into the corresponding cyclic ethers (2-alkyl- or 2-aryl-6-bromo-2,3-dihydrofuro[3,2-b]pyridines. Similar chemistry, in which epoxides (instead of aldehydes) are used in reaction with the pyridylmethyl carbanion, leads to 2-alkyl- and 2-aryl-7-bromo-2,3-dihydropyrano[3,2-b]pyridines. These 2-substituted, brominated dihydrofuro- and dihydropyranopyridines are also substrates for the Heck reaction. For instance, 6-bromo-2,3-dihydro-2-phenylfuro[3,2-b]pyridine can be coupled, in a palladium catalyzed process, with N-methyl-N-(tert-butoxycarbonyl)-4-penten-2-amine, and the coupling product treated with trifluoroacetic acid (to remove the tert-butoxycarbonyl group), to give (4E)-N-methyl-5-(6-(2,3-dihydro-2-phenylfuro[3,2-b]pyridin)yl)-4-penten-2-amine.

The 5-bromo-2-methyl-3-pyridinol, required for the syntheses of the brominated dihydrofuro- and dihydropyranopyridines, is produced by standard transformations of commercially available materials. Thus, 2-methyinicotinic acid (Aldrich Chemical Company) can be converted, by sequential treatment with thionyl chloride, bromine, and ammonia (methodology described by C. V. Greco et al., *J. Heterocyclic Chem.* 7: 761–766 (1970)), into 5-bromo-2-methylnicotinamide. Hofmann rearrangement of 5-bromo-2-methylnicotinamide with hypochlorite will give 3-amino-5-bromo-2-methylpyridine, which can be converted to 5-bromo-2-methyl-3-pyridinol by diazotization with sodium nitrite in aqueous sulfuric acid. Alternatively, alanine ethyl ester (Aldrich Chemical Company) is converted (using ethyl formate) into its N-formyl derivative, which is then converted to 5-ethoxy-4-methyloxazole using phosphorous pentoxide (N. Takeo et al., Japan Patent No. 45,012,732). Diels-Alder reaction of 5-ethoxy-4-methyloxazole with acrylonitrile gives 5-hydroxy-6-methylnicotinonitrile (T. Yoshikawa et al., *Chem. Pharm. Bull.* 13: 873 (1965)), which is converted to 5-amino-2-methyl-3-pyridinol by hydration (nitrite ⇒ amide) and Hofmann rearrangement (Y. Morisawa et al., *Agr. Biol. Chem.* 39: 1275–1281 (1975)). The 5-amino-2-methyl-3-pyridinol can then be converted, by diazotization in the presence of cuprous bromide, to the desired 5-bromo-2-methyl-3-pyridinol.

Alternatively, the aryl substituted olefinic amine compounds of the present invention can be prepared by coupling an N-protected aminoaldehyde, such as 4-(N-methyl-N-(tert-butoxycarbonyl)amino)pentanal with an aryllithium. The required aldehyde can be prepared according to methodology described by Otsuka et al., *J. Am Chem. Soc.* 112: 838–845 (1990), starting from commercially available 1,5-dimethyl-2-pyrrolidinone (Aldrich Chemical Company). Thus, heating 1,5-dimethyl-2-pyrrolidinone with 6N hydrochloric acid forms 4-(methylamino)pentanoic acid, which can be readily esterified to ethyl 4-(methylamino)pentanoate. The latter compound can be treated with one equivalent of di-tert-butyl dicarbonate to give ethyl 4-(N-methyl-N-(tert-butoxycarbonyl)amino)pentanoate which is then reduced with DIBAL-H to give 4-(N-methyl-N-(tert-butoxycarbonyl)amino)pentanal. Reaction of this aldehyde with an aryllithium generates an alcohol, which can subsequently be converted to the N-protected olefinic amine by conversion of the alcohol to the alkyl halide (with, for instance, carbon tetrachloride and triphenylphosphine) and subsequent dehydrohalogenation (with 1,8-diazabicyclo[5.4.0]undec-7-ene). Removal of the tert-butoxycarbonyl protecting group, with trifluoroacetic acid, affords the desired (E)-5-aryl-4-penten-2-amine. Thus, 3-lithio-5-isopropoxypyridine (from 3-bromo-5-isopropoxypyridine and n-butyllithium) can be condensed with 4-(N-methyl-N-(tert-butoxycarbonyl)amino)pentanal to give 1-(3-(5-isopropoxypyridin)yl)-4-(N-methyl-N-(tert-butoxycarbonyl)amino)-1-pentanol, which can subsequently be converted into (4E)-N-methyl-5-(3-(5-isopropoxypyridin)yl)-4-penten-2-amine.

The R and S enantiomers of 1,5-dimethyl-2-pyrrolidinone can be made from commercially available (R)- and (S)-5-(hydroxymethyl)-2-pyrrolidinone (Aldrich Chemical Company). Thus, reaction of the enantiomerically pure hydroxymethylpyrrolidinone with carbon tetrabromide and triphenylphosphine in acetonitrile gives the corresponding 5-(bromomethyl)-2-pyrrolidinone (Pfaltz et al., *Helv. Chim. Acta* 79: 961 (1996)), which is reduced to the 5-methylpyrrolidinone by tri-n-butyltin hydride in toluene (Otsuka et al., *J. Amer. Chem. Soc.* 112: 838 (1990)). Subsequent methylation using sodium hydride and methyl iodide in tetrahydrofuran gives the enantiomerically pure 1,5-dimethyl-2-pyrrolidinone.

The methods by which enantiomerically pure 4-(N-methyl-N-(tert-butoxycarbonyl)amino)pentanal is synthesized can vary. Using methodology similar to that reported by Schessinger et al., *Tetrahedron Lett.* 28: 2083–2086 (1987), either N-methyl-L-alanine or N-methyl-D-alanine (available from Sigma) can be reacted sequentially with lithium aluminum hydride (to give the corresponding N-methylaminopropanols), di-tert-butyl dicarbonate (to protect the amino group), and p-toluenesulfonyl chloride (to esterify the alcohol). The resulting (S)- or (R)-1-p-toluenesulfonyloxy-N-methyl-N-(tert-butoxycarbonyl)-2-propanamine can be used to alkylate lithium acetylide to give the corresponding (S)- or (R)-N-methyl-N-(tert-butoxycarbonyl)-4-pentyn-2-amines. These, in turn, can be hydroborated and oxidized, by methods described by H. C. Brown et al., *J. Amer. Chem. Soc.* 97: 5249 (1975), to give (S)- or (R)-4-(N-methyl-N-(tert-butoxycarbonyl)amino)pentanal.

Fused ring heterocycles can also be lithiated and condensed with 4-(N-methyl-N-(tert-butoxycarbonyl)amino) pentanal. For example, 6-chloro-2-phenylfuro[3,2-b] pyridine can be treated sequentially with n-butyllithium and with 4-(N-methyl-N-(tert-butoxycarbonyl)amino)pentanal to give 1-(6-(2-phenylfuro[3,2-b]pyridin)yl)-4-(N-methyl-N-(tert-butoxycarbonyl)amino)-1-pentanol. Conversion of the alcohol to the alkyl halide, and subsequent dehydrohalogention and deprotection, gives (4E)-N-methyl-5-(6-(2-phenylfuro[3,2-b]pyridin)yl)-4-penten-2-amine. The requisite 6-chloro-2-phenylfuro[3,2-b]pyridine can be produced, using methodology similar to that described by A. Arcadi et al., *Synthesis*, 749 (1986), in which 5-chloro-2-iodo-3-pyridinol is reacted with phenylacetylene in the presence of palladium(II) acetate and cuprous iodide. In turn, the 5-chloro-2-iodo-3-pyridinol can be made by iodination of commercially available 5-chloro-3-pyridinol (Aldrich Chemical Company) using methods described by V. Koch et al., *Synthesis*, 497 (1990).

The compositions of the present invention are aryl substituted ammonium salt compositions that possess anions derived from 2,3-diacyltartaric acids. Acids of this type have the general formula shown below, where R''' and R'''' are alkyl (preferably lower alkyl), substituted alkyl, aryl, substituted aryl, heterocyclyl, or substituted heterocyclyl (as those terms are defined hereinbefore).

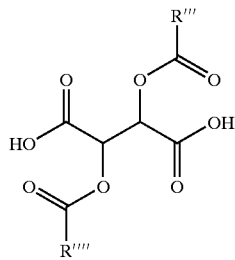

Acids of the 2,3-diacyltartaric type occur as stereoisomers at carbons 2 and 3. Thus, for those cases in which R''' and R'''' are identical, a DL pair (enantiomeric pair) and a meso compound exist. The D isomer has the S,S absolute configuration, and the L isomer has the R,R absolute configuration. The meso compound has the R,S absolute configuration. For those cases in which R''' and R'''' are different from one another, two enantiomeric pairs exist, an R,R/S,S pair and an R,S/S,R pair. The present invention relates to the use of any of these stereoisomeric acids in conjunction with aryl substituted amines in salt preparations. In certain preferred embodiments of the present invention, R''' and R'''' are each phenyl and either the D or the L isomer of the acid is used, but it is most preferred that R''' and R'''' are each p-tolyl and either the D or the L isomer of the acid is used.

The stoichiometry of the salts comprising the present invention can vary. It is typical that the molar ratio of acid (2,3-diacyltartaric type) to base (aryl substituted amine type) is 1:2 or 1:1, but other ratios (such as 3:2 and 2:1) are possible. It is preferred that the molar ratio of acid to base be 1:2. Depending upon the manner by which the salts of the present invention are formed, those salts may have crystal structures that may occlude solvents that are present during salt formation. Thus, salts of the present invention can occur as hydrates and other solvates of varying stoichiometry of solvent relative to aryl substituted amine.

A number of acyltartaric acids can be combined with aryl substituted amines to form salt compounds of the present invention. These acyltartaric acids are either commercially available (e.g., dibenzoyl-L-tartaric acid, dibenzoyl-D-tartaric acid, di-p-toluoyl-L-tartaric acid, di-p-toluoyl-D-tartaric acid, dipivaloyl-L-tartaric acid, and dipivaloyl-D-tartaric acid from Aldrich) or can be readily synthesized according to the method described by Furuta et al., *Org. Syn.* Coll. Vol VII, 722–727 (1990). Thus the preparation of acyltartaric acids begins with esterification of either D- or L-tartaric acid with benzyl alcohol, to provide dibenzyl D- or L-tartrate. Treatment of either dibenzyl tartrate with two equivalents of an organic acid chloride provides the corresponding dibenzyl 2,3-diacyltartrate. Subsequent hydrogenolysis of the dibenzyl esters using hydrogen and palladium on charcoal generates the 2,3-diacyltartaric acids in which both acyl groups are the same. Treatment of dibenzyl tartrate with one equivalent of an acid chloride provides, after hydrogenolysis, a 2-acyltartaric acid. Alternatively, successive treatment of dibenzyl tartrate with one equivalent of each of two different acid chlorides affords the unsymmetrical dibenzyl 2,3-diacyltartrate, which upon hydrogenolysis provides the unsymmetrical 2,3-diacyltartaric acid. These procedures can utilize D-, L- or meso-tartaric acid as starting material.

The method for providing compounds of the present invention can vary. The preparation of (2S)-(4E)-N-methyl-5-[3-(5-isopropoxypyridin)yl)]-4-penten-2-amine in a di-p-toluoyl-D-tartrate form involves (i) adding a solution of suitably pure compound dissolved in ethanol to a solution of di-p-toluoyl-L-tartaric acid (0.5–1 equivalents) in ethanol, heated under reflux, to form a precipitate, (ii) applying heat and/or water and ethanol (water not to exceed 10%) to dissolve the precipitate, (iii) cooling the resulting solution if necessary to cause precipitation of the salt and (iv) filtering and collecting the salt. The stoichiometry, solvent mix, solute concentration and temperature employed can vary. The acylated tartaric acids to be used in the present invention for salt formation include: di-benzoyl-L-tartaric acid, di-benzoyl-D-tartaric acid, di-p-toluoyl-L-tartaric acid, di-p-toluoyl-D-tartaric acid, di-pivaloyl-L-tartaric acid and di-pivaloyl-D-tartaric acid which are commercially available (Aldrich Chemical Company) or di-o-toluoyl-L-tartaric acid, di-o-toluoyl-D-tartaric acid, di-m-toluoyl-L-tartaric acid, di-m-toluoyl-D-tartaric acid, di-p-methoxybenzoyl-L-tartaric acid, di-p-methoxybenzoyl-D-tartaric acid, di-o-methoxybenzoyl-L-tartaric acid, di-o-methoxybenzoyl-D-tartaric acid, di-m-methoxybenzoyl-L-tartaric acid, di-m-methoxybenzoyl-D-tartaric acid, di-p-bromobenzoyl-L-tartaric acid, di-p-bromobenzoyl-D-tartaric acid, di-o-bromobenzoyl-D-tartaric acid, di-o-bromobenzoyl-L-tartaric acid, di-m-bromobenzoyl-D-tartaric acid and di-m-bromobenzoyl-L-tartaric acid which are readily synthesized from dibenzyltartrate and two equivalents of the appropriate acid chloride followed by hydrogenation to remove the benzyl protecting groups. Alternatively, the di-t-butylacetyl tartrate, di-butyryl tartrate and di-i-valeryl tartrate as described in U.S. Pat. No. 5,326,782 to Barriere et al. can be utilized as the counterion. See, also, U.S. Pat. Nos. 5,962, 737 to 4,803,207 to White et al. and U.S. Pat. No. 4,528,290 to Wong et al.

The present invention relates to a method for providing prevention of a condition or disorder to a subject susceptible to such a condition or disorder, and for providing treatment to a subject suffering therefrom. For example, the method comprises administering to a patient an amount of a compound effective for providing some degree of prevention of the progression of a CNS disorder (i.e., provide protective effects), amelioration of the symptoms of a CNS disorder, and amelioration of the reoccurrence of a CNS disorder. The method involves administering an effective amount of a compound selected from the general formulae which are set forth hereinbefore. The present invention relates to a pharmaceutical composition incorporating a compound selected from the general formulae which are set forth hereinbefore. The present invention also relates to prodrug derivatives of the compounds of the present invention. The compounds normally are not optically active. However, certain compounds can possess substituent groups of a character so that those compounds possess optical activity. Optically active compounds can be employed as racemic mixtures or as enantiomers.

The salts of the present invention which are derived from aryl substituted amines and 2,3-diacyl-tartaric acids have a number of advantages over other salts derived from aryl substituted amines and other acids, such as fumaric acid or galactaric acid. In general, the 2,3-diacyl-tartaric acid salts of aryl substituted amines are water-soluble materials that tend to be more crystalline and less hygroscopic in nature than other salts. For example, the di-p-toluoyl-D-tartrate salt of (2S)-(4E)-N-methyl-5-[3-(5-isopropoxypyridin)yl)]-4-penten-2-amine is water soluble, highly crystalline, non-polymorphic and is less hygroscopic than the corresponding salt derived from galactaric acid (mucic acid). For instance, the amount of water absorbed at 40° C. and 70% relative humidity by the hemigalactarate of (2S)-(4E)-N-methyl-5-[3-(5-isopropoxypyridin)yl)]-4-penten-2-amine was 11.8% whereas the amount of water absorbed by the corresponding hemi-(di-p-toluoyl-D-tartrate) at room temperature and 90% relative humidity was 3.2%. As such, the di-p-toluoyl-D-tartrate salt of (2S)-(4E)-N-methyl-5-[3-(5-isopropoxypyridin)yl)]-4-penten-2-amine is a free-flowing crystalline powder; and such a property is a definite advantage for pharmaceutical formulation development and pharmaceutical manufacturing. If necessary, this salt can be milled to an acceptable particle size range for pharmaceutical processing. The di-p-toluoyl-D-tartrate salt of (2S)-(4E)-N-methyl-5-[3-(5-isopropoxypyridin)yl)]-4-penten-2-amine has a high melting point and is physically and chemically stable and non-reactive. The salt is compatible with a wide range of excipients that might be chosen for the manufacture of solid oral dosage forms. This is especially so for those exicipients, such polysaccharide derivatives, that are pharmaceutically defined hydrates and those with only loosely bound surface water. As an illustration, salts derived from certain aryl substituted amines, such as E-metanicotine and fumaric acid are prone to the formation of impurities within the salt. For example, impurities arise from the Michael addition reaction of the secondary amine in E-metanicotine to the olefin in fumaric acid. These impurities lower the chemical purity of the salt and adversely affect the chemical integrity of the salt upon long-term storage. The acid component of the above salt—di-p-toluoyl-D-tartaric acid has been used on numerous occasions as a resolving agent for non-racemic amines producing salts of high optical purity. In the case of the above non-racemic amine, (2S)-(4E)-N-methyl-5-[3-(5-isopropoxypyridin)yl)]-4-penten-2-amine, the formation of the corresponding di-p-toluoyl-D-tartaric acid salt will lead to a salt of increased optical purity. The increased optical purity can lead to a more pure nicotinic agonist and consequently an increase in binding affinity for certain nicotinic receptors.

Compounds of the present invention are useful for treating those types of conditions and disorders for which other types of nicotinic compounds have been proposed as therapeutics. See, for example, Williams et al. *DN&P* 7(4):205–227 (1994), Arneric et al., *CNS Drug Rev.* 1(1):1–26 (1995), Arneric et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al the disclosures of which are incorporated herein by reference in their entirety. Compounds of the present invention can be used as analgesics, to treat ulcerative colitis, to treat a variety of neurodegenerative diseases, and to treat convulsions such as those that are symtematic of epilepsy. CNS disorders which can be treated in accordance with the present invention include presenile dementia (early onset Alzheimer's disease), senile dementia (dementia of the Alzheimer's type), HIV-dementia, multiple cerebral infarcts, Parkinsonism including Parkinson's disease, Pick's disease, Huntington's chorea, tardive dyskinesia, hyperkinesia, mania, attention deficit disorder, anxiety, depression, mild cognitive impairment, dyslexia, schizophrenia and Tourette's syndrome. Compounds of the present invention also can be used to treat conditions such as syphillis and Creutzfeld-Jakob disease. The compounds are administered using known techniques. The compositions of the present invention also can be administered in formulation compositions that incorporate other ingredients, such as those types of ingredients that are useful in formulating a diagnostic composition. Compositions as diagnostics are employed as set forth in U.S. Pat. No. 5,853,696 to Elmalch et al. and U.S. Pat. No. 5,969,144 to London et al. Salts of the present invention are desirably useful in therapeutic applications. See, for example, Berge et al., *J. Pharm. Sci.*, 66: 1–19 (1977) and Anderson et al., In: *The Practice Medicinal Chemistry*, Ch. 34: 739–754 (1996).

The compositions can be administered in the form of a prodrug. "Prodrug" means a compound which is rapidly transformed in vivo to yield the parent peptide compound, for example by hydrolysis in blood. "Pharmaceutically acceptable prodrug" means a compound which is, within the scope of sound medical judgment, suitable for pharmaceutical use in a patient without undue toxicity, irritation, allergic response, and the like, and effective for the intended use, including a pharmaceutically acceptable ester as well as a zwitterionic form, where possible, of the peptide compounds of the invention. Pharmaceutically acceptable prodrugs according to the invention are described in T.Higuchi and V. Stella, Pro-drugs as Novel Delivery Systems, Vol.14 of the A.C.S. Symposium Series, and in Edward B. Roche, ed., Bioreversible Carriers in Drug Design, American Pharmaceutical Association and Pergamon Press, 1987, both of which are incorporated herein by reference.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compositions are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compositions in the form of a bulk active chemical, it is preferred to present each compound in the form of a pharmaceutical composition or formulation for efficient and effective administration. Exemplary methods for administering such compounds will be apparent to the skilled artisan. For example, the compositions can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that effect the functioning of the CNS. More specifically, in treating a CNS disorder administration preferably is such so as to optimize the effect upon those relevant receptor subtypes which have an effect upon the functioning of the CNS, while minimizing the effects upon muscle-type receptor subtypes. Other suitable methods for administering the compositions of the present invention are described in U.S. Pat. No. 5,604,231 to Smith et al.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to activatie relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular effects are observed.

Typically, the effective dose of compounds generally requires administering the compound in an amount of less than 5 mg/kg of patient weight. Often, the compounds of the present invention are administered in an amount from less than about 1 mg/kg patent weight, and usually less than about 100 ug/kg of patient weight, but frequently between about 10 ug to less than 100 ug/kg of patient weight. For compounds of the present invention that do not induce effects on muscle type nicotinic receptors at low concentrations, the effective dose is less than 5 mg/kg of patient weight; and often such compounds are administered in an amount from 50 ug to less than 5 mg/kg of patient weight. The foregoing effective doses typically represent that amount administered as a single dose, or as one or more doses administered over a 24 hour period.

For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 500, often does not exceed about 400, and frequently does not exceed about 300 ug/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds, which are useful in carrying out the present invention are generally greater than about −0.5, often are greater than about 0, and frequently are greater than about 0.5. The log P values of such typical compounds generally are less than about 3, often are less than about 2, and frequently are less than about 1. Log P values provide a measure of the ability of a compound to pass across a diffusion barrier, such as a biological membrane. See, Hansch, et al., *J. Med. Chem.* 11:1 (1968).

The compounds useful according to the method of the present invention have the ability to bind to, and in most circumstances, cause activation of, nicotinic dopaminergic receptors of the brain of the patient. As such, such compounds have the ability to express nicotinic pharmacology, and in particular, to act as nicotinic agonists. The receptor binding constants of typical compounds useful in carrying out the present invention generally exceed about 0.1 nM, often exceed about 1 nM, and frequently exceed about 10 nM. The receptor binding constants of certain compounds are less than about 100 uM, often are less than about 10 uM and frequently are less than about 5 uM; and of preferred compounds generally are less than about 1 uM, often are less than about 100 nM, and frequently are less than about 50 nM. Though not preferred, certain compounds possess receptor binding constants of less than 10 uM, and even less than 100 uM. Receptor binding constants provide a measure of the ability of the compound to bind to half of the relevant receptor sites of certain brain cells of the patient. See, Cheng, et al., *Biochem. Pharmacol.* 22:3099 (1973).

The compounds useful according to the method of the present invention have the ability to demonstrate a nicotinic function by effectively activating neurotransmitter secretion from nerve ending preparations (i.e., synaptosomes). As such, such compounds have the ability to activate relevant neurons to release or secrete acetylcholine, dopamine, and other neurotransmitters. Generally, typical compounds useful in carrying out the present invention provide for the activation of dopamine secretion in amounts of at least one third, typically at least about 10 times less, frequently at least about 100 times less, and sometimes at least about 1,000 times less, than those required for activation of muscle-type nicotinic receptors. Certain compounds of the present invention can provide secretion of dopamine in an amount which is comparable to that elicited by an equal molar amount of (S)-(−)-nicotine.

The compounds of the present invention, when employed in effective amounts in accordance with the method of the present invention, are selective to certain relevant nicotinic receptors, but do not cause significant activation of receptors associated with undesirable side effects at concentrations at least greater than those required for activation of dopamine release. By this is meant that a particular dose of compound resulting in prevention and/or treatment of a CNS disorder, is essentially ineffective in eliciting activation of certain muscle-type nicotinic receptors at concentration higher than 5 times, preferably higher than 100 times, and more preferably higher than 1,000 times, than those required for activation of dopamine release. This selectivity of certain compounds of the present invention against those ganglia-type receptors responsible for cardiovascular side effects is demonstrated by a lack of the ability of those compounds to activate nicotinic function of adrenal chromaffin tissue at concentrations greater than those required for activation of dopamine release.

Compounds of the present invention, when employed in effective amounts in accordance with the method of the present invention, are effective towards providing some degree of prevention of the progression of CNS disorders, amelioration of the symptoms of CNS disorders, an amelioration to some degree of the reoccurrence of CNS disorders. However, such effective amounts of those compounds are not sufficient to elicit any appreciable side effects, as demonstrated by increased effects relating to skeletal muscle. As such, administration of certain compounds of the present invention provides a therapeutic window in which treatment of certain CNS disorders is provided, and certain side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less than 1/5, and often less than 1/10 that amount sufficient to cause certain side effects to any significant degree.

The pharmaceutical compositions of the present invention can be employed to prevent or treat certain other conditions, diseases and disorders. Exemplary of such diseases and disorders include inflammatory bowel disease, acute cholangitis, aphteous stomatitis, arthritis (e.g., rheumatoid arthritis and ostearthritis), neurodegenerative diseases, cachexia secondary to infection (e.g., as occurs in AIDS, AIDS related complex and neoplasia), as well as those indications set forth in PCT WO 98/25619. The pharmaceutical compositions of the present invention can be employed in order to ameliorate may of the symptoms associated with those conditions, diseases and disorders. Thus, pharmaceutical compositions of the present invention can be used in treating genetic diseases and disorders, in treating autoimmune disorders such as lupus, as anti-infectious agents (e.g, for treating bacterial, fungal and viral infections, as well as the effects of other types of toxins such as sepsis), as anti-inflammatory agents (e.g., for treating acute cholangitis, aphteous stomatitis, asthma, and ulcerative colitis), and as inhibitors of cytokines release (e.g., as is desirable in the treatment of cachexia, inflammation, neurodegenerative diseases, viral infection, and neoplasia), The compounds of the present invention can also be used as adjunct therapy in combination with existing therapies in the management of the aforementioned types of diseases and disorders. In such situations, administration preferably is such that the active ingredients of the pharmaceutical formulation act to optimize effects upon abnormal cytokine production, while minimizing effects upon receptor subtypes such as those that are associated with muscle and ganglia. Administration preferably is such that active ingredients interact with regions where cytokine production is affected or occurs. For the treatment of such conditions or disorders, compounds of the present invention are very potent (i.e., affect cytokine production and/or secretion at very low concentrations), and are very efficacious (i.e., significantly inhibit cytokine production and/or secretion to a relatively high degree).

Effective doses are most preferably at very low concentrations, where maximal effects are observed to occur. Concentrations, determined as the amount of compound per volume of relevant tissue, typically provide a measure of the degree to which that compound affects cytokine production. Typically, the effective dose of such compounds generally requires administering the compound in an amount of much less than 100 ug/kg of patient weight, and even less than 1 u/kg of patient weight. The foregoing effective doses typically represent the amount administered as a single dose, or as one or more doses administered over a 24 hour period.

For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 1, often does not exceed about 0.75, often does not exceed about 0.5, frequently does not exceed about 0.25 mg/24 hr./patient. In addition, administration of the effective dose is such that the concentration of the compound within the plasma of the patient normally does not exceed 500 pg/ml, often does not exceed 300 pg/ml, and frequently does not exceed 100 pg/ml. When employed in such a manner, compounds of the present invention are dose dependent, and as such, cause inhibition of cytokine production and/or secretion when employed at low concentrations but do not exhibit those inhibiting effects at higher concentrations. Compounds of the present invention exhibit inhibitory effects upon cytokine production and/or secretion when employed in amounts less than those amounts necessary to elicit activation of relevant nicotinic receptor subtypes to any significant degree.

The following examples are provided to illustrate the present invention, and should not be construed as limiting thereof. In these examples, all parts and percentages are by weight, unless otherwise noted.

EXAMPLES

Example 1
Determination of Binding to Relevant Receptor Sites

Binding of the compounds to relevant receptor sites was determined in accordance with the techniques described in U.S. Pat. No. 5,597,919 to Dull et al. Inhibition constants (Ki values), reported in nM, were calculated from the $IC_{50}$ values using the method of Cheng et al., *Biochem, Pharmacol.* 22:3099 (1973). Low binding constants indicate that the compounds of the present invention exhibit good high affinity binding to certain CNS nicotinic receptors.

Example 2

Sample No. 1 is (2S)-(4E)-N-methyl-5-[3-(5-isopropoxypyridin)yl]-4-penten-2-amine hemi-(di-p-toluoyl-L-tartrate) and is prepared as follows:

(2S)-(4E)-N-Methyl-5-[3-(5-isopropoxypyridin)yl]-4-penten-2-amine was prepared according to the procedure described in PCT WO 99/65876 to Caldwell et al.

(2S)-(4E)-N-Methyl-5-[3-(5-isopropoxypyridin)yl]-4-penten-2-amine hemi-(di-p-toluoyl-L-tartrate) is prepared using the following procedure: A solution of (2S)-(4E)-N-methyl-5-[3-(5-isopropoxypyridin)yl]-4-penten-2-amine (0.2466 g, 1.052 mmol) in absolute ethanol (6 mL) was added drop-wise to a stirring solution of di-p-toluoyl-L-tartaric acid (0.4066 g, 1.052 mmol) in absolute ethanol (5 mL) maintained at near reflux. The resulting light-yellow solution was allowed to cool to ambient temperature and was allowed to stand for 15 h. No solids had precipitated. Therefore, the solution was concentrated by rotary evaporation, followed by drying under high vacuum. The resulting off-white foam was dissolved in isopropanol (3 mL), assisted by heating to near reflux. Upon cooling to ambient temperature, diethyl ether (3 mL) was added drop-wise. The resulting mixture was kept at 5° C. for 16 h. The resulting solids were filtered, washed with diethyl ether and vacuum dried at 40° C. to afford 0.2383 g (53.0%) of a white powder. A 0.167 g portion of this material was dissolved in a minimum amount of ethyl acetate, assisted by heating. The resulting solution was allowed to cool to ambient temperature and was further cooled at 5° C. The resulting solids were filtered, washed with ethyl acetate and vacuum dried at 40° C. to afford 0.1393 g (83.4% recovery) of a white powder, mp 159–161° C.

Sample No. 1 exhibited a Ki of 6 nM. The low binding constant indicates that the compound has a good binding affinity for certain CNS nicotinic receptors.

Example 3

Sample No. 2 is (2S)-(4E)-N-methyl-5-[3-(5-isopropoxypyridin)yl]-4-penten-2-amine hemi-(di-p-toluoyl-D-tartrate) and is prepared as follows:

(2S)-(4E)-N-Methyl-5-[3-(5-isopropoxypyridin)yl]-4-penten-2-amine hemi-(di-p-toluoyl-D-tartrate) was prepared as follows: A solution of (2S)-(4E)-N-methyl-5-[3-(5-isopropoxypyridin)yl]-4-penten-2-amine (0.1272 g, 0.54 mmol) (prepared as described above) in absolute ethanol (3 mL) was added drop-wise to a stirring solution of di-p-toluoyl-D-tartaric acid (0.085 g, 0.219 mmol) in absolute ethanol (3 mL) maintained at near reflux. The yellow solution was allowed to cool to room temperature for 2 h, cooled to 0° C. for 1 h, and the resulting solids were collected by filtration. The solids were vacuum dried at 40° C. to afford 0.1695 g (73.0%) of a white powder, mp 197–201° C.

Sample No. 2 exhibited a Ki of 5 nM. The low binding constant indicates that the compound has a good binding affinity for certain CNS nicotinic receptors.

Example 4

Sample No. 2, (2S)-(4E)-N-methyl-5-[3-(5-isopropoxypyridin)yl]-4-penten-2-amine hemi-(di-p-toluoyl-D-tartrate) can be provided according to the following procedure: Methanol (50 mL) was added to a solution of (2S)-(4E)-N-methyl-5-[3-(5-isopropoxypyridin)yl]-4-penten-2-amine (prepared as described above) in t-butyl methyl ether (TBME) (165.5 g of solution containing 19.4 g (82.8 mmol) of free base). The mixture was heated and TBME and methanol were distilled out whilst adding methanol simultaneously to maintain the volume. A total of 225 mL was both added and distilled. The batch was cooled to about 40° C. and di-p-toluoyl-D-tartaric acid (19.2 g) was added forming a precipitate. The mixture was weighed to determine the quantity of methanol present. Further methanol (33 mL) was added to adjust the concentration of the salt to 14% w/w. The mixture was heated until a solution was formed (about 68° C.) and was then cooled to the crystallization point. Methanol (137 mL) was distilled out under reduced pressure whilst adding an equal volume of isopropanol. The slurry was cooled to 0–5° C. (over 45 minutes). The resulting product was filtered off, washed with chilled isopropanol (25 mL) and dried at 50° C. in vacuo to yield (2S)-(4E)-N-methyl-5-[3-(5-isopropoxypyrid in)yl]-4-penten-2-amine hemi-(di-p-toluoyl-D-tartrate) (32.6 g; 92.1%).

Example 5

Sample No. 3 is (E)-Metanicotine mono-(di-p-toluoyl-L-tartrate), which is provided as follows:

(E)-Metanicotine was prepared from nicotine according to the procedure described in U.S. Pat. No. 5,663,356 to Ruecroft and Woods.

(E)-Metanicotine mono-(di-p-toluoyl-L-tartrate) was provided as follows: A stirred solution of di-p-toluoyl-L-tartaric acid (0.491 g, 1.233 mmol) in tetrahydrofuran (THF) (3.7 mL) and ethanol (0.8 mL) was heated at reflux under a nitrogen atmosphere as a solution of (E)-metanicotine (0.200 g, 0.1.233 mmol) in THF (1 mL) was added drop-wise over a 3 min period. The mixture was allowed to cool to ambient temperature and then stored at 5° C. for 48 h. The precipitate was filtered, washed with cold THF-ethanol (9:1 v/v) (2×1 mL), followed by cold THF (2×3 mL) and then vacuum dried at 40° C. for 3 h to give 0.642 g (94.9%) of a white powder. The material was recrystallized by dissolving in hot ethanol (5 mL), filtration of the hot solution through glass wool, and cooling of the filtrate to ambient temperature and then at 5° C. for 24 h. The resulting solids were filtered, washed with cold ethanol (2×2 mL) and vacuum dried at 45° C. for 24 h to give 0.575 g (91.0% recovery for an overall yield of 85.1%) of a white powder, mp 157.5–159.5° C.

Sample No. 3 exhibited a Ki of 14 nM. The low binding constant indicates that the compound has a good binding affinity for certain CNS nicotinic receptors.

The foregoing is illustrative of the present invention and is not to be construed as limiting thereof. The invention is defined by the following claims, with equivalents of the claims to be included therein.

That which is claimed is:

1. A compound of the formula:

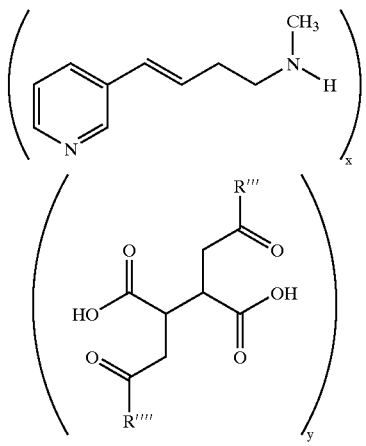

wherein x is an integer from 1 to 2, y is an integer from 1 to 3, with the proviso that x is 2 when y is 3, and R''' and R'''' are alkyl or substituted alkyl and have one to eight carbons.

2. The compound according to claim 1, wherein x and y are 1.

3. The compound according to claim 1, wherein the compound of formula:

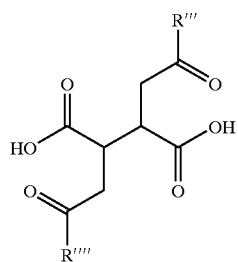

is selected from the group consisting of di-benzoyl-L-tartaric acid, di-benzoyl-D-tartaric acid, di-p-toluoyl-L tartaric acid, di-p-toluoyl-D-tartaric acid, di-pivaloyl-L-tartaric acid, di-pivaloyl-D-tartaric acid, di-o-toluoyl-L-tartaric acid, di-o-toluoyl-D-tartaric acid, di-m-toluoyl-L-tartaric acid, di-m-toluoyl-D-tartaric acid, di-p-methoxybenzoyl-L-tartaric acid, di-p-methoxybenzoyl-D-tartaric acid, di-o-methoxybenzoyl-L-tartaric acid, di-o-methoxybenzoyl-D-tartaric acid, di-m-methoxybenzoyl-L-tartaric acid, di-m-methoxybenzoyl-D-tartaric acid, di-p-bromobenzoyl-L-tartaric acid, di-p-bromobenzoyl-D-tartaric acid, di-o-bromobenzoyl-D-tartaric acid, di-o-bromobenzoyl-L-tartaric acid, di-m-bromobenzoyl-D-tartaric acid and di-m-bromobenzoyl-L-tartaric acid.

4. A pharmaceutical composition comprising:
a) an effective amount of a compound of the formula

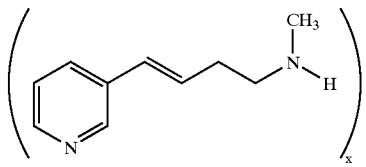

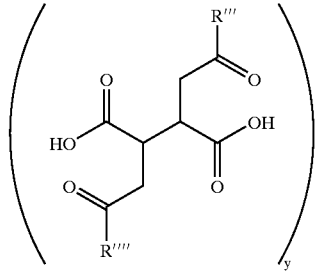

wherein x is an integer from 1 to 2, y is an integer from 1 to 3, with the proviso that x is 2 when y is 3, and R''' and R'''' are alkyl or substituted alkyl and have one to eight carbons, and b) a pharmaceutically acceptable, inert carrier.

5. The pharmaceutical composition according to claim 4, wherein x and y are 1.

6. The composition according to claim 4, wherein the compound of formula:

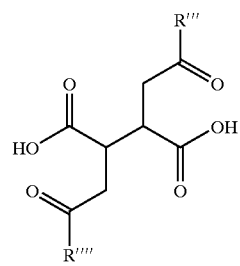

is selected from the group consisting of di-benzoyl-L-tartaric acid, di-benzoyl-D-tartaric acid, di-p-toluoyl-L tartaric acid, di-p-toluoyl-D-tartaric acid, di-pivaloyl-L-tartaric acid, di-pivaloyl-D-tartaric acid, di-o-toluoyl-L-tartaric acid, di-o-toluoyl-D-tartaric acid, di-m-toluoyl-L-tartaric acid, di-m-toluoyl-D-tartaric acid, di-p-methoxybenzoyl-L-tartaric acid, di-p-methoxybenzoyl-D-tartaric acid, di-o-methoxybenzoyl-L-tartaric acid, di-o-methoxybenzoyl-D-tartaric acid, di-m-methoxybenzoyl-L-tartaric acid, di-m-methoxybenzoyl-D-tartaric acid, di-p-bromobenzoyl-L-tartaric acid, di-p-bromobenzoyl-D-tartaric acid, di-o-bromobenzoyl-D-tartaric acid, di-o-bromobenzoyl-L-tartaric acid, di-m-bromobenzoyl-D-tartaric acid and di-m-bromobenzoyl-L-tartaric acid.

7. A method for treating a disorder that results from an alteration in normal neurotransmitter release comprising administering to a subject in need thereof an effective amount of a composition comprising a compound of the formula

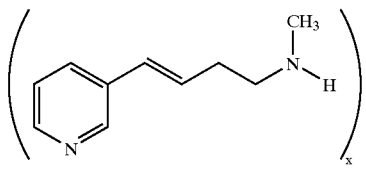

-continued

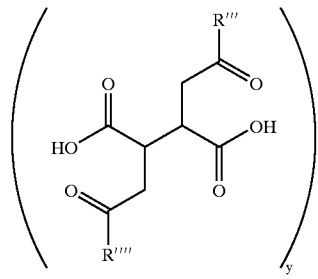

wherein x is an integer from 1 to 2, y is an integer from 1 to 3, with the proviso that x is 2 when y is 3, and R''' and R'''' are alkyl or substituted alkyl and have one to eight carbons.

8. The method according to claim 4, wherein x and y are 1.

9. The method according to claim 7, wherein the compound of formula:

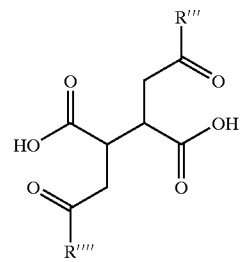

is selected from the group consisting of di-benzoyl-L-tartaric acid, di-benzoyl-D-tartaric acid, di-p-toluoyl-L tartaric acid, di-p-toluoyl-D-tartaric acid, di-pivaloyl-L-tartaric acid, di-pivaloyl-D-tartaric acid, di-o-toluoyl-L-tartaric acid, di-o-toluoyl-D-tartaric acid, di-m-toluoyl-L-tartaric acid, di-m-toluoyl-D-tartaric acid, di-p-methoxybenzoyl-L-tartaric acid, di-p-methoxybenzoyl-D-tartaric acid, di-o-methoxybenzoyl-L-tartaric acid, di-o-methoxybenzoyl-D-tartaric acid, di-m-methoxybenzoyl-L-tartaric acid, di-m-methoxybenzoyl-D-tartaric acid, di-p-bromobenzoyl-L-tartaric acid, di-p-bromobenzoyl-D-tartaric acid, di-o-bromobenzoyl-D-tartaric acid, di-o-bromobenzoyl-L-tartaric acid, di-m-bromobenzoyl-D-tartaric acid and di-m-bromobenzoyl-L-tartaric acid.

* * * * *

UNITED STATES PATENT AND TRADEMARK OFFICE
CERTIFICATE OF CORRECTION

PATENT NO. : 6,743,812 B1
DATED : June 1, 2004
INVENTOR(S) : Gary Maurice Dull

It is certified that error appears in the above-identified patent and that said Letters Patent is hereby corrected as shown below:

Column 29,
Lines 10 and 30, the formulae should appear as follows:

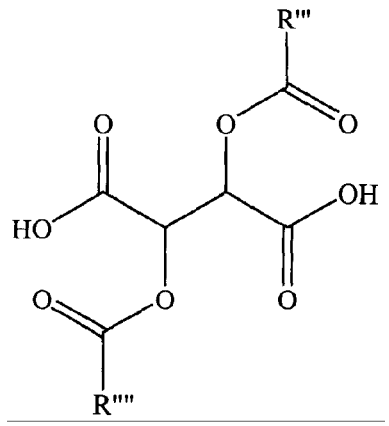

Column 30,
Lines 5 and 25, the formulae should appear as follows:

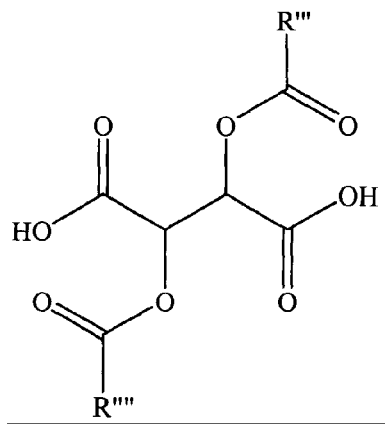

UNITED STATES PATENT AND TRADEMARK OFFICE
CERTIFICATE OF CORRECTION

PATENT NO. : 6,743,812 B1
DATED : June 1, 2004
INVENTOR(S) : Gary Maurice Dull

It is certified that error appears in the above-identified patent and that said Letters Patent is hereby corrected as shown below:

Column 30 (cont'd),
Lines 54-55, the phrase "a disorder that results from an alteration in normal neurotransmitter release" should read -- pain, ulcerative colitis, convulsions, presenile dementia, senile dementia, HIV-dementia, multiple cerebral infarcts, Parkinsonism, Pick's disease, Huntington's chorea, tardive dyskinesia, hyperkinesias, mania, attention deficit disorder, anxiety, depression, mild cognitive impairment, dyslexia, schizophrenia, or Tourette's syndrome".

Column 31,
Line 5, the formulae should appear as follows:

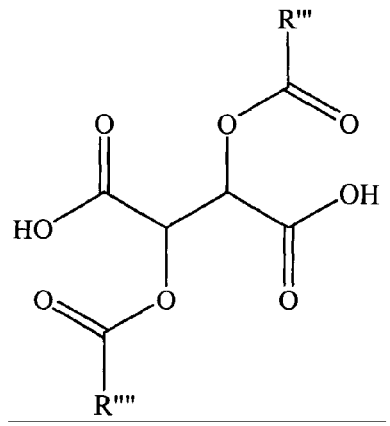

Lines 21 and 22, should read as follows:
-- The method according to claim 7, wherein x and y are 1. --.

UNITED STATES PATENT AND TRADEMARK OFFICE
CERTIFICATE OF CORRECTION

PATENT NO.   : 6,743,812 B1
DATED         : June 1, 2004
INVENTOR(S)  : Gary Maurice Dull It is certified that error appears in the above-identified patent and that said Letters Patent is hereby corrected as shown below:

Column 32,
Line 5, the formulae should appear as follows:

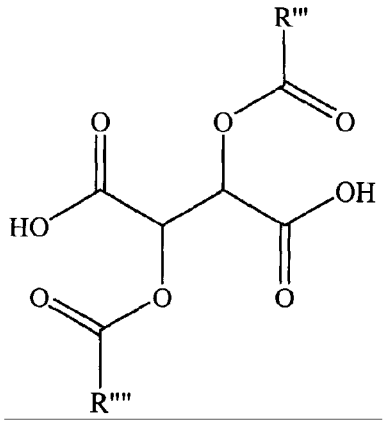

Signed and Sealed this

Twenty-fifth Day of October, 2005

JON W. DUDAS
*Director of the United States Patent and Trademark Office*